(12) United States Patent
Meschkat et al.

(10) Patent No.: US 11,395,534 B2
(45) Date of Patent: Jul. 26, 2022

(54) HANDHELD TREATMENT APPARATUS WITH NOZZLE SEALING ASSEMBLY

(71) Applicant: The Procter & Gamble Company, Cincinnati, OH (US)

(72) Inventors: Stephan Meschkat, Bad Soden (DE); Faiz Feisal Sherman, Mason, OH (US); Tobias Reimann, Alzey (DE)

(73) Assignee: The Procter & Gamble Company, Cincinnati, OH (US)

( * ) Notice: Subject to any disclaimer, the term of this patent is extended or adjusted under 35 U.S.C. 154(b) by 398 days.

(21) Appl. No.: 16/689,128

(22) Filed: Nov. 20, 2019

(65) Prior Publication Data

US 2020/0196733 A1 Jun. 25, 2020

Related U.S. Application Data

(60) Provisional application No. 62/782,592, filed on Dec. 20, 2018.

(51) Int. Cl.
*A45D 34/04* (2006.01)
*A45D 40/26* (2006.01)
(Continued)

(52) U.S. Cl.
CPC ............ *A45D 34/041* (2013.01); *A61B 5/441* (2013.01); *A45D 40/261* (2013.01);
(Continued)

(58) Field of Classification Search
CPC .... A45D 34/041; A45D 40/261; A45D 34/04; A45D 40/26; A45D 2040/00;
(Continued)

(56) References Cited

U.S. PATENT DOCUMENTS 2,249,832 A * 7/1941 Hubschman ........... B65D 47/18
401/262
3,078,497 A * 2/1963 Micallef ................ A45D 34/04
401/148
(Continued)

FOREIGN PATENT DOCUMENTS

| GB | 2511770 A | 9/2014 |
|---|---|---|
| WO | 2007064722 A1 | 6/2007 |
| WO | WO2015180115 A1 | 12/2015 |

OTHER PUBLICATIONS

All Office Actions; U.S. Appl. No. 16/689,129.
(Continued)

*Primary Examiner* — David J Walczak
(74) *Attorney, Agent, or Firm* — Steven Robert Chuey; Sarah M DeCristofaro

(57) ABSTRACT

An apparatus for treating human skin includes an outer housing including a graspable portion, an applicator head and a cartridge connected to the applicator head. The cartridge includes a nozzle located in the applicator head. An image capture device captures images of the human skin through an opening in the applicator head. A processor analyzes the images of the human skin to identify skin deviations. A sealing assembly includes a support portion and a resiliently deformable sealing element supported by the support portion at a location within the applicator head. The sealing assembly has a closed configuration where the sealing element is sealed against the nozzle and an open configuration where the sealing element is removed outward away from the nozzle in a composition delivery direction to expose the nozzle for operation.

13 Claims, 20 Drawing Sheets

(51) Int. Cl.
*A45D 34/00* (2006.01)
*A61B 5/00* (2006.01)
*A61B 18/00* (2006.01)

(52) U.S. Cl.
CPC .. *A45D 2034/005* (2013.01); *A45D 2200/051* (2013.01); *A45D 2200/20* (2013.01); *A61B 2018/00452* (2013.01)

(58) Field of Classification Search
CPC ........ A45D 2040/0006; A45D 2200/05; A45D 2200/051; A45D 2200/10; A45D 2200/20; A45D 2034/002; A45D 2034/005; A61B 5/441; A61B 2018/00452; A61B 5/444; A61B 5/44
USPC .................................. 401/261, 262, 195, 218
See application file for complete search history.

(56) References Cited

U.S. PATENT DOCUMENTS

| | | | |
|---|---|---|---|
| 5,533,823 A * | 7/1996 | Pierpont | A45C 13/008 401/262 |
| 7,367,648 B2 | 5/2008 | Karppinen | |
| 7,370,936 B2 | 5/2008 | Karppinen | |
| 7,384,119 B2 | 6/2008 | Karppinen | |
| 7,387,358 B2 | 6/2008 | Karppinen | |
| 7,399,054 B2 | 7/2008 | Morgan | |
| 7,399,057 B2 | 7/2008 | Morgan | |
| 7,401,886 B2 | 7/2008 | Karppinen | |
| 7,401,887 B2 | 7/2008 | Karppinen | |
| 7,401,888 B2 | 7/2008 | Karppinen | |
| 7,413,281 B2 | 8/2008 | Karppinen | |
| 7,425,049 B2 | 9/2008 | Morgan | |
| 7,425,051 B2 | 9/2008 | Morgan | |
| 7,438,381 B2 | 10/2008 | Morgan | |
| 7,438,382 B2 | 10/2008 | Morgan | |
| 7,441,863 B2 | 10/2008 | Morgan | |
| 7,445,310 B2 | 11/2008 | Morgan | |
| 7,448,720 B2 | 11/2008 | Morgan | |
| 7,448,722 B2 | 11/2008 | Morgan | |
| 7,448,723 B2 | 11/2008 | Morgan | |
| 7,472,981 B2 | 1/2009 | Morgan | |
| 7,506,952 B2 | 3/2009 | Karppinen | |
| 7,506,958 B2 | 3/2009 | Morgan | |
| 7,575,297 B2 | 8/2009 | Morgan | |
| 7,686,419 B2 | 3/2010 | Morgan | |
| 7,695,097 B2 | 4/2010 | Morgan | |
| 7,753,470 B2 | 7/2010 | Karppinen | |
| 7,753,472 B2 | 7/2010 | Morgan | |
| 7,753,479 B2 | 7/2010 | Karppinen | |
| 7,806,502 B2 | 10/2010 | Karppinen | |
| 7,832,828 B2 | 11/2010 | Karppinen | |
| 7,857,417 B2 | 12/2010 | Morgan | |
| 7,862,144 B2 | 1/2011 | Morgan | |
| 7,891,760 B2 | 2/2011 | Karppinen | |
| 7,922,285 B2 | 4/2011 | Karppinen | |
| 7,938,503 B2 | 5/2011 | Morgan | |
| 7,976,122 B2 | 7/2011 | Morgan | |
| 8,083,313 B2 | 12/2011 | Karppinen | |
| 8,100,517 B2 | 1/2012 | Karppinen | |
| 8,113,619 B2 | 2/2012 | Morgan | |
| 8,118,393 B2 | 2/2012 | Karppinen | |
| 8,118,397 B2 | 2/2012 | Morgan | |
| 8,123,332 B2 | 2/2012 | Morgan | |
| 8,136,918 B2 | 3/2012 | Morgan | |
| 8,205,959 B2 | 6/2012 | Morgan | |
| 8,398,202 B2 | 3/2013 | Karppinen | |
| 2007/0080986 A1 | 4/2007 | Karppinen | |
| 2007/0080987 A1 | 4/2007 | Karppinen | |
| 2007/0080988 A1 | 4/2007 | Karppinen | |
| 2007/0080990 A1 | 4/2007 | Karppinen | |
| 2007/0080991 A1 | 4/2007 | Morgan | |
| 2007/0080995 A1 | 4/2007 | Morgan | |
| 2007/0080996 A1 | 4/2007 | Morgan | |
| 2007/0080997 A1 | 4/2007 | Morgan | |
| 2007/0080998 A1 | 4/2007 | Morgan | |
| 2007/0080999 A1 | 4/2007 | Morgan | |
| 2007/0081000 A1 | 4/2007 | Morgan | |
| 2007/0081001 A1 | 4/2007 | Morgan | |
| 2007/0081002 A1 | 4/2007 | Karppinen | |
| 2007/0081003 A1 | 4/2007 | Karppinen | |
| 2007/0081004 A1 | 4/2007 | Morgan | |
| 2007/0081005 A1 | 4/2007 | Morgan | |
| 2007/0081006 A1 | 4/2007 | Morgan | |
| 2007/0081007 A1 | 4/2007 | Morgan | |
| 2007/0081015 A1 | 4/2007 | Karppinen | |
| 2007/0081016 A1 | 4/2007 | Karppinen | |
| 2007/0081021 A1 | 4/2007 | Morgan | |
| 2007/0081022 A1 | 4/2007 | Morgan | |
| 2007/0081023 A1 | 4/2007 | Morgan | |
| 2007/0081024 A1 | 4/2007 | Morgan | |
| 2007/0081025 A1 | 4/2007 | Morgan | |
| 2007/0081026 A1 | 4/2007 | Karppinen | |
| 2008/0158286 A1 | 7/2008 | Karppinen | |
| 2008/0158287 A1 | 7/2008 | Karppinen | |
| 2008/0238981 A1 | 10/2008 | Morgan | |
| 2008/0238985 A1 | 10/2008 | Karppinen | |
| 2008/0238986 A1 | 10/2008 | Karppinen | |
| 2008/0238991 A1 | 10/2008 | Morgan | |
| 2008/0246798 A1 | 10/2008 | Karppinen | |
| 2008/0246799 A1 | 10/2008 | Karppinen | |
| 2008/0246800 A1 | 10/2008 | Karppinen | |
| 2008/0246802 A1 | 10/2008 | Karppinen | |
| 2008/0291237 A1 | 11/2008 | Morgan | |
| 2008/0291238 A1 | 11/2008 | Morgan | |
| 2009/0002434 A1 | 1/2009 | Morgan | |
| 2009/0002436 A1 | 1/2009 | Morgan | |
| 2009/0002437 A1 | 1/2009 | Morgan | |
| 2009/0009557 A1 | 1/2009 | Morgan | |
| 2009/0015631 A1 | 1/2009 | Morgan | |
| 2009/0021554 A1 | 1/2009 | Morgan | |
| 2009/0021555 A1 | 1/2009 | Morgan | |
| 2009/0085962 A1 | 4/2009 | Morgan | |
| 2009/0141072 A1 | 6/2009 | Morgan | |
| 2009/0147041 A1 | 6/2009 | Karppinen | |
| 2009/0147042 A1 | 6/2009 | Silverbrook | |
| 2009/0147043 A1 | 6/2009 | Mcavoy | |
| 2009/0147046 A1 | 6/2009 | Morgan | |
| 2009/0278885 A1 | 11/2009 | Morgan | |
| 2009/0289988 A1 | 11/2009 | Karppinen | |
| 2010/0171790 A1 | 7/2010 | Morgan | |
| 2010/0182373 A1 | 7/2010 | Morgan | |
| 2010/0271442 A1 | 10/2010 | Karppinen | |
| 2010/0277543 A1 | 11/2010 | Morgan | |
| 2010/0277544 A1 | 11/2010 | Karppinen | |
| 2012/0045270 A1 | 2/2012 | Apodaca | |
| 2014/0371690 A1 | 12/2014 | Sprada | |
| 2016/0022011 A1 | 1/2016 | Rabe | |

OTHER PUBLICATIONS

International Search Report and Written Opinion, PCT/US2019/062312, dated Feb. 20, 2020, 13 pgs.
International Search Report and Written Opinion, PCT/US2019/062313, dated Feb. 5, 2020, 11 pgs.

* cited by examiner

HANDHELD TREATMENT APPARATUS WITH NOZZLE SEALING ASSEMBLY

FIELD

The present application relates to a handheld treatment apparatus for applying compositions to skin, and other keratinous surfaces and, in particular, a handheld treatment apparatus that includes a nozzle sealing assembly.

BACKGROUND

Tonal variations on human skin have multiple causes. Acne, freckles, sun damage, and age spots are just a few of the common causes of visible defects on skin. Textural variations such as fine lines, wrinkles and scars are also well known. Both tonal and textural deviations are noticeable to the human eye, even when they are quite small. Covering large areas of skin on and around deviations with makeup or other concealers is known.

Skin treatment apparatuses have been proposed that can analyze images of human skin and deliver skin treatment compositions based on the images. The skin treatment apparatuses may include a compartment that houses the skin treatment compositions and a delivery component that is used to deliver the skin treatment compositions to the skin. As can be appreciated, maintenance may be needed for the apparatuses to operate effectively.

SUMMARY

In an embodiment, an apparatus for treating human skin includes an outer housing including a graspable portion, an applicator head and a cartridge connected to the applicator head. The cartridge includes a nozzle located in the applicator head. An image capture device captures images of the human skin through an opening in the applicator head. A processor analyzes the images of the human skin to identify skin deviations. A sealing assembly includes a support portion and a resiliently deformable sealing element supported by the support portion at a location within the applicator head. The sealing assembly has a closed configuration where the sealing element is sealed against the nozzle and an open configuration where the sealing element is removed outward away from the nozzle in a composition delivery direction to expose the nozzle for operation.

In another embodiment, a method of activating an apparatus for treating human skin is provided. The method includes placing a cartridge assembly within an outer housing. The cartridge assembly includes an applicator head and a cartridge connected to the applicator head. The cartridge includes a nozzle located in the applicator head. A sealing assembly is moved comprising a support portion and a resiliently deformable sealing element from a closed configuration where the sealing element is sealed against the nozzle to an open configuration where the sealing element is removed outward away from the nozzle in a composition delivery direction to expose the nozzle for operation. Images of the human skin are captured through an opening in the applicator head using an image capture device. The images of the human skin are analyzed to identify skin deviations using a processor. A skin treatment composition is delivered from the nozzle onto the human skin.

In another embodiment, a cartridge assembly for a handheld skin treatment apparatus includes an image capture device that captures images of the human skin and a processor that analyzes the images of the human skin to identify skin deviations. The cartridge assembly includes an applicator head and a cartridge connected to the applicator head, the cartridge comprising a nozzle located in the applicator head. A sealing assembly includes a support portion and a resiliently deformable sealing element supported by the support portion at a location within the applicator head. The sealing assembly has a closed configuration where the sealing element is sealed against the nozzle and an open configuration where the sealing element is removed outward away from the nozzle in a composition delivery direction to expose the nozzle for operation.

Embodiments described herein can solve many problems with prior devices and methods. Specifically, the handheld treatment devices lock a cap of a cartridge assembly of the handheld treatment devices to an applicator head when the cartridge assembly is removed from the handheld treatment device. While locked to the applicator head, the cap closes a sealing assembly to seal a sealing element against nozzles of a nozzle array, which helps to improve operation of the nozzle array once the cartridge assembly is connected to the handheld treatment apparatus. Further, the cartridge assembly can be removed from the handheld treatment apparatus only when the cap is connected to the applicator head, which again closes the sealing assembly.

BRIEF DESCRIPTION OF THE DRAWINGS

While the specification concludes with claims particularly pointing out and distinctly claiming the present invention, it is believed the same will be better understood from the following description taken in conjunction with the accompanying drawing in which:

DETAILED DESCRIPTION

Embodiments described herein may be understood more readily by reference to the following detailed description. It is to be understood that the scope of the claims is not limited to the specific compositions, methods, conditions, devices, or parameters described herein, and that the terminology used herein is not intended to be limiting. Also, as used in the specification, including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent basis "about," it will be understood that the particular values form another embodiment. All ranges are inclusive and combinable.

Figure 1:
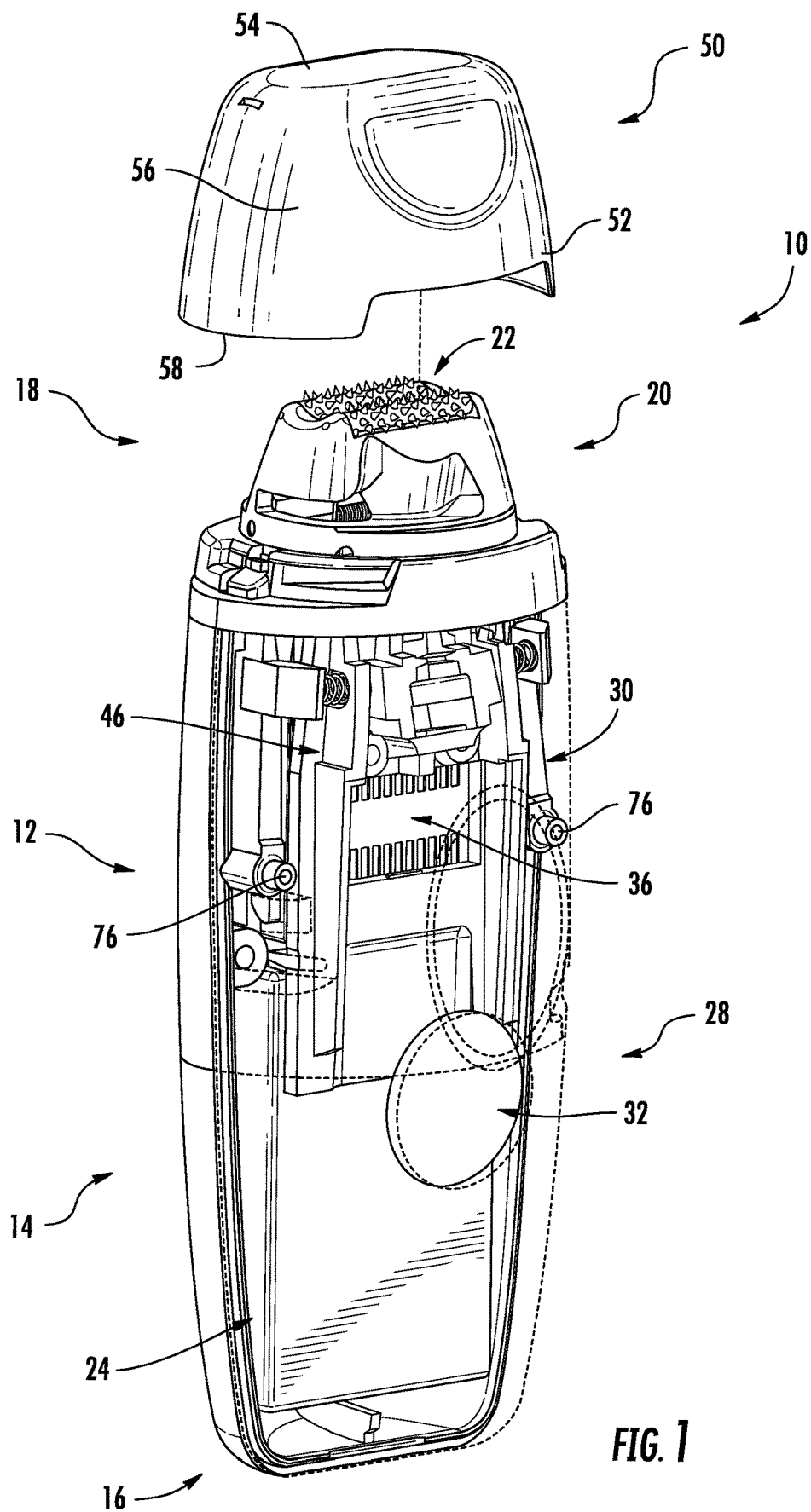
FIG. 1 illustrates a perspective view of a handheld treatment apparatus, according to one or more embodiments described herein.

Referring to FIG. 1, a handheld treatment apparatus 10 for applying compositions to skin generally includes an outer housing 12, which is shown transparent for illustrative purposes that is sized and shaped to be held in-hand and manipulated manually during a treatment operation. The outer housing 12 includes a graspable portion 14 including a base 16 and an applicator portion 18 including an applicator head 20 having an opening 22 through which a skin treatment composition can be delivered to the skin. A battery 24 (e.g., a rechargeable battery) may be located in the graspable portion 14 of the outer housing 12. In other embodiments, the handheld treatment apparatus 10 may not include a battery or the handheld treatment apparatus 10 may be plugged, for example, to an electrical supply outlet. In some embodiments, the graspable portion 14 including the base 16 may include lighting for illuminating the base 16 or other locations of the outer housing 12. A user interface 28 may also be provided where a user can provide inputs or control instructions to a processing unit 30 for controlling the handheld treatment apparatus 10. While various buttons or touch areas 32 (e.g., utilizing capacitive touch sensors, momentary switches, etc.) are illustrated for the user to touch and activate, any other suitable input devices may be used, such as touch screen displays, voice commands, etc. Acoustics and haptics may be provided to provide user information during use regarding usage conditions. In some embodiments, the handheld treatment apparatus 10 may be capable of wireless communication and be controlled remotely, e.g., using a cell phone or other handheld computing device, or capable of otherwise sending information wirelessly or wired to an external device, for example, for tracking treatment results.

The applicator portion 18 may include the applicator head 20 including the opening 22 through which the skin treatment composition can be delivered to the skin and a cartridge 36 that is located within the outer housing 12. As will be described in greater detail below, the cartridge 36 may include a nozzle array that is embedded in a cartridge die. In other embodiments, separate nozzles may be used that can be connected to the cartridge. The applicator head 20 can provide a space between the skin surface at the opening 22 and the nozzle array (and other components) during use. An image capture device 46 may also be located at the applicator portion 18 and adjacent the cartridge 36. The image capture device 46 can be any of a variety of commercially available devices such as a digital camera. The image capture device 46 takes a picture of the skin and sends it to the processing unit 30. The processing unit 30 may be generally referred to as a central processing unit, or CPU, which may comprise a simple circuit board, a more complex computer, or the like. The image may be analyzed by the processing unit 30 to identify skin deviations. A pen driver may be provided to facilitate communication with the processing unit 30 with external devices (e.g., for tracking treatments, such as skin tone affects, time of use, etc.) A variety of lighting may also be provided to illuminate the skin area such that the image capture device can have constant illumination. The lighting can be, for example, a diode, incandescent light or any other suitable light source.

A cap 50 may be provided that can interlock with the applicator head 20 and/or outer housing 12. The cap 50 generally includes a cap body 52 having a cover wall 54 and a side wall 56 that extends outward from the cover wall 54 to an edge 58. As will be described in greater detail below, the cap 50 may have a closed and locked configuration that allows for removal of the cartridge 36 from the outer housing 12 and a closed and unlocked configuration that allows for removal of the cap from the applicator head 20 and use of the handheld treatment apparatus 10 with cartridge 36. The outer housing 12, applicator head 20 and cap 50 will now be described in greater detail.

Applicator Head and Cap Locking and Unlocking

Figure 2:
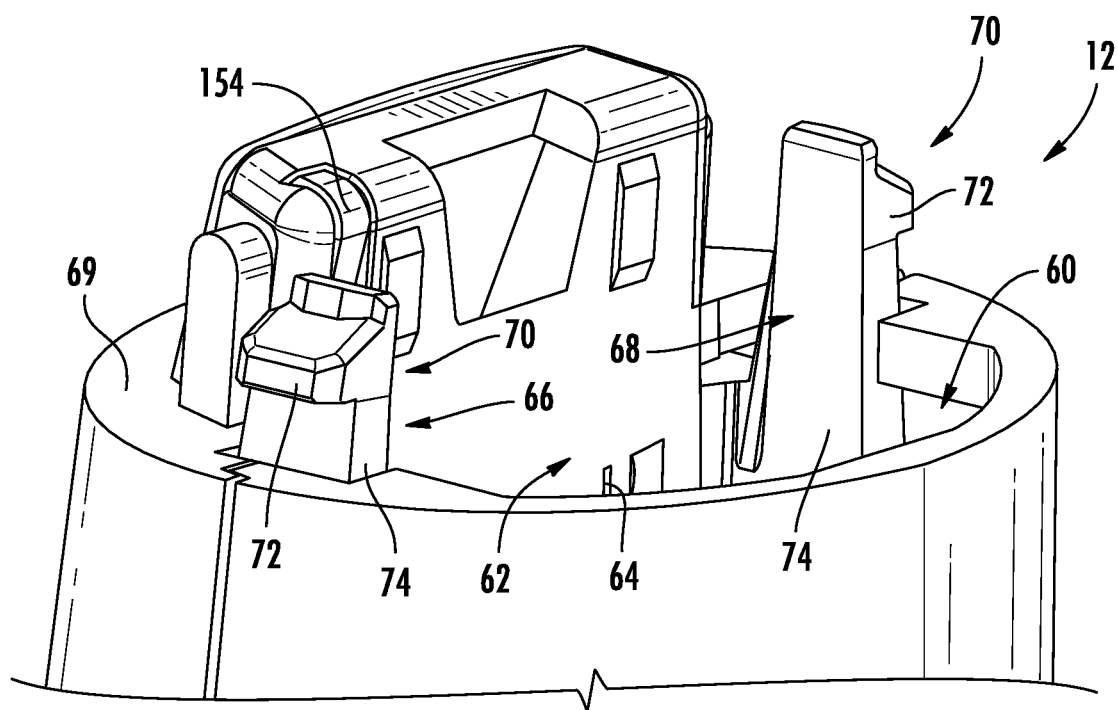
FIG. 2 illustrates a perspective view of an outer housing of the handheld treatment apparatus of FIG. 1, according to one or more embodiments shown and described herein.

Referring to FIG. 2, the outer housing 12 is illustrated without the applicator head 20, cartridge 36 and cap 50. The outer housing 12 includes a cartridge receiving volume 60 and a cartridge identifying device 62 that is located at the cartridge receiving volume 60. The cartridge identifying device 62 may be shaped and sized to provide the cartridge receiving volume 60 with a cross-sectional shape that receives the cartridge 36 in only a single, predetermined angular orientation that allows for identification of the cartridge 36 using, for example, electrical contacts 64 or other suitable sensor, such as a switch, hall magnetic sensor, optical sensor, etc.

The outer housing 12 further includes a pair of applicator head engagement structures 66 and 68 that extend outward beyond a terminal edge 69 of the outer housing 12. In the illustrated example, the applicator head engagement structures 66 and 68 include hook members 70 including a head 72 and an arm 74 that extends axially from the head and into the outer housing 12. In some embodiments, the arms 74 may be movably connected to the outer housing at locations 76 (FIG. 1) that allow the arms 74 to provide a spring-like biasing force that biases the heads 72 outwardly away from a central axis of the outer housing 12 (i.e., in a lateral direction). The arms 74 also allow the heads 72 to resiliently move inwardly toward the central axis of the outer housing 12, which can allow for releasing the applicator head 20 from the outer housing 12. In some embodiments, the applicator head engagement structures 66 and 68 may be formed separately from the outer housing 12 and connected thereto. In other embodiments, one or both of the applicator head engagement structures 66 and 68 may be formed as a monolithic part of the outer housing 12, e.g., using a molding process.

Figure 3:
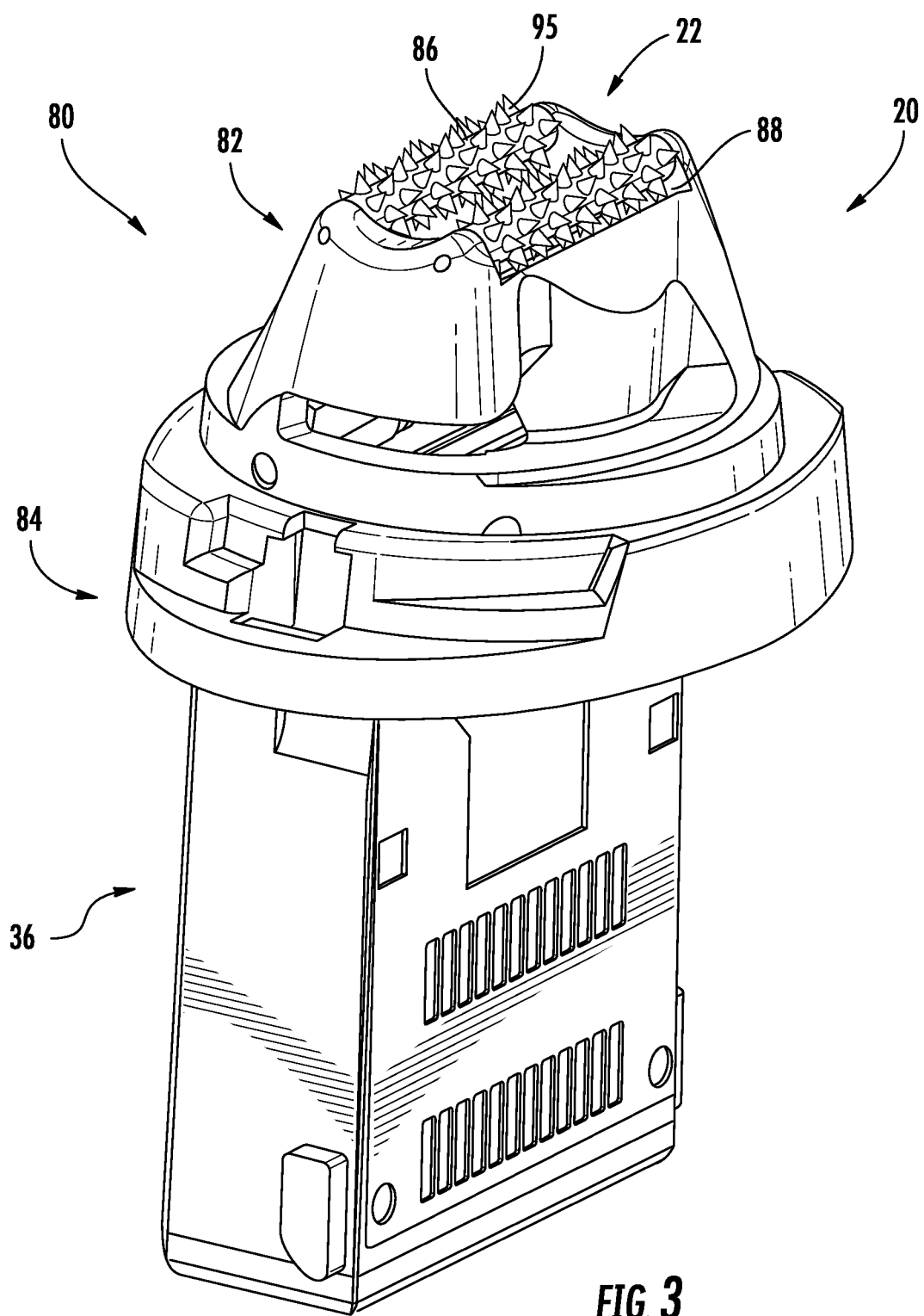
FIG. 3 is a perspective view of a cartridge assembly of the handheld treatment apparatus of FIG. 1, according to one or more embodiments shown and described herein.

Referring to FIG. 3, the cartridge 36 is illustrated connected to the applicator head 20, thereby forming a cartridge assembly 80. In this example, the cartridge assembly 80 may be formed so as to fix the cartridge 36 to the applicator head 20. As used herein, the term "fix" means intended to not be removed without damage. The term "fixed" is not meant to exclude the ability of the applicator head 20 to move (e.g., rotate) relative to the cartridge 36 while remaining connected thereto. The cartridge assembly 80 may be, for example, packaged together as a refill for the handheld treatment apparatus 10. In other embodiments, the cartridge 36 may be provided separately from the applicator head 20.

Figure 4:
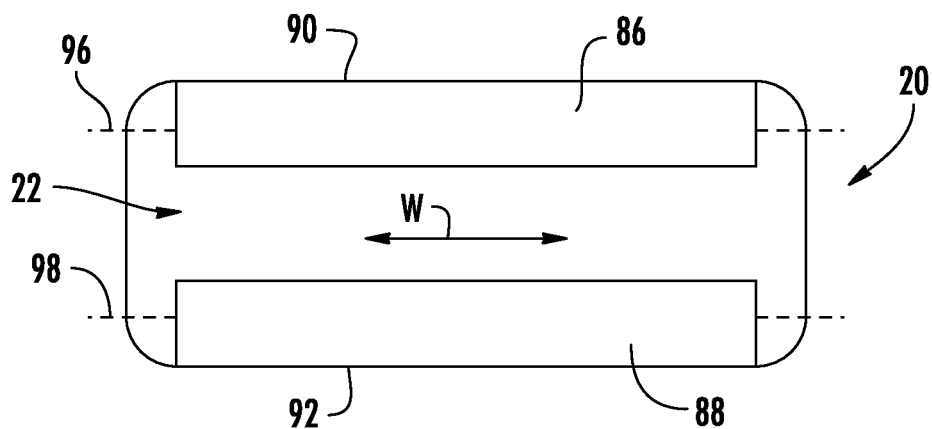
FIG. 4 is a diagrammatic plan view of an applicator head of the handheld treatment apparatus of FIG. 1, according to one or more embodiments shown and described herein.

The applicator head 20 includes a head portion 82 and a socket portion 84. The head portion 82 extends outward from the socket portion 84 in the axial direction to the opening 22 at an apex of the head portion 82. In some embodiments, one or more skin engagement members, in this example, rollers 86 and 88 may be provided at the opening 22. The rollers 86 and 88 may be provided for a number of reasons including to maintain contact between the handheld treatment apparatus 10 and the skin surface, to influence friction between the skin and the handheld treatment apparatus 10 while moving the handheld treatment apparatus 10 across the skin, to present a relatively flat skin surface to the image capture device 46 and nozzle array, and to detect movement and/or speed of movement on skin. FIG. 4 illustrates the rollers 86 and 88 in isolation with the opening 22 formed in the applicator head 20. In this embodiment, the rollers 86 and 88 are located at opposite edges 90 and 92 of the opening 22, extending continuously across a width W of the opening 22. In this way, the rollers 86 and 88 define forward and rearward rolling directions perpendicular to their axes of rotation 96 and 98 for the handheld treatment apparatus 10 where the rollers 86 and 88 can be rolled over the skin surface. In some embodiments, the opening 22 has an area that is less than 100 mm$^2$.

As illustrated, the rollers 86 and 88 may be continuous along their entire lengths and each roll as a single unit. In other embodiments, multiple rollers may be used along the edges 90 and 92, capable of independent rotation. The rollers 86 and 88 may have a surface feature that can be used to increase contact between the surface of the rollers 86 and 88 and the skin surface (e.g., to reduce smearing or displacement of the skin treatment composition). For example, the rollers 86 and 88 may be provided with projections 95 (FIG. 3) to provide peaks that roll against the skin surface. Any other suitable surface features may be used, such as frusto-conical projections, grooves, etc. that allow for rolling against the skin while presenting a relatively flat skin surface within the opening 22. The rollers 86 and 88 may be formed of any suitable materials, such as plastic or rubber and randomly formed materials such as foam, sintered, flocked or sputtered materials.

Figure 5:
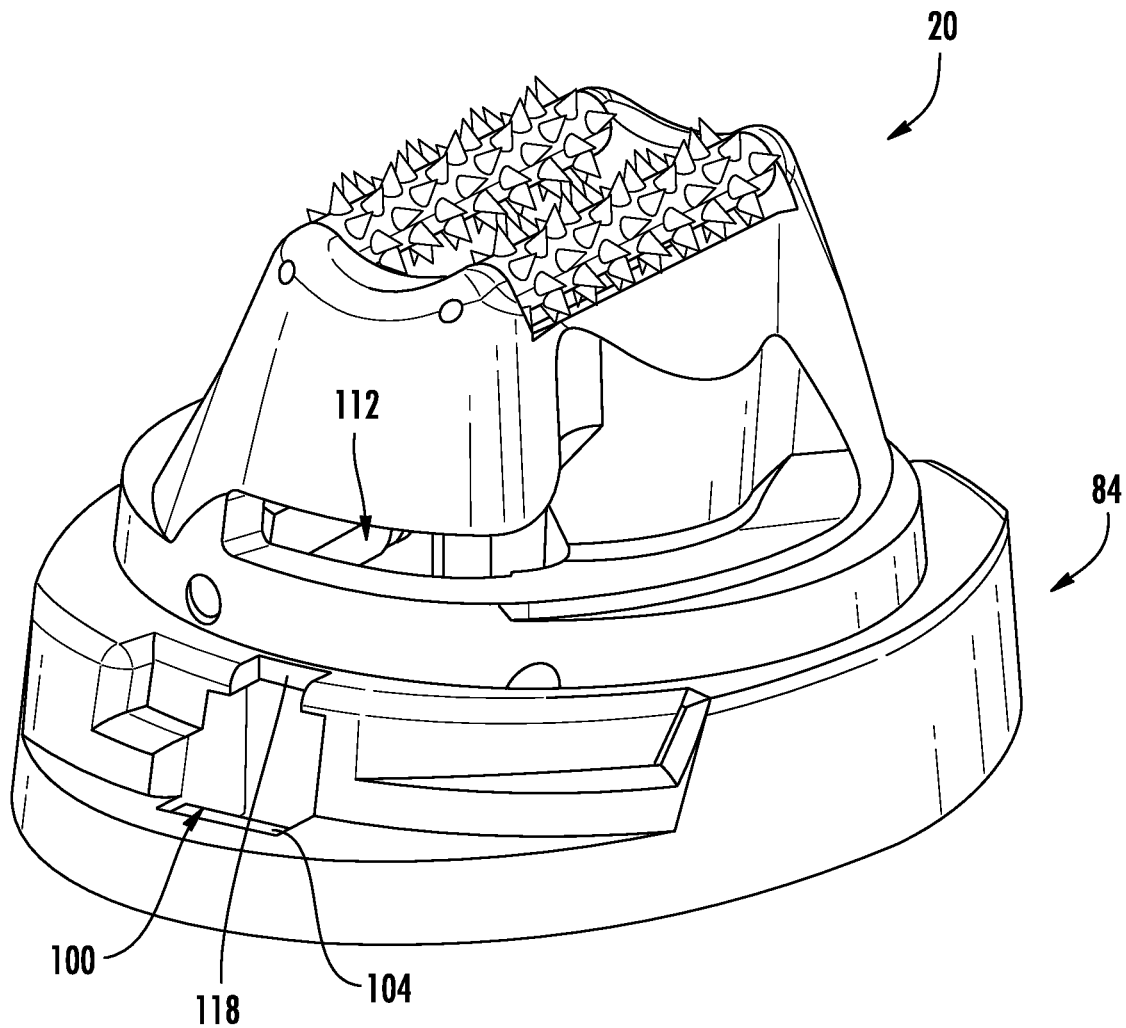
FIG. 5 is a perspective view of an applicator head of the handheld treatment apparatus of FIG. 1, according to one or more embodiments shown and described herein.
Figure 6:
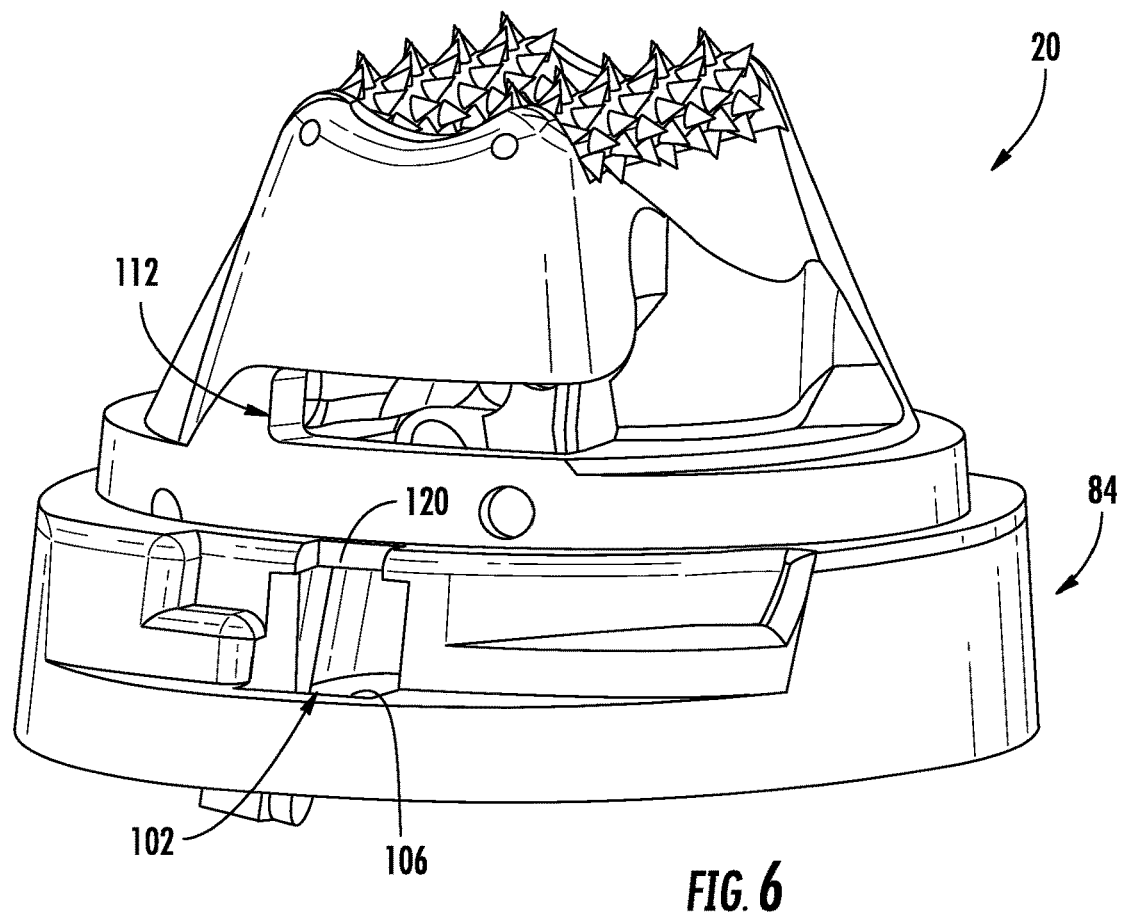
FIG. 6 is another perspective view of the applicator head of FIG. 5.
Figure 7:
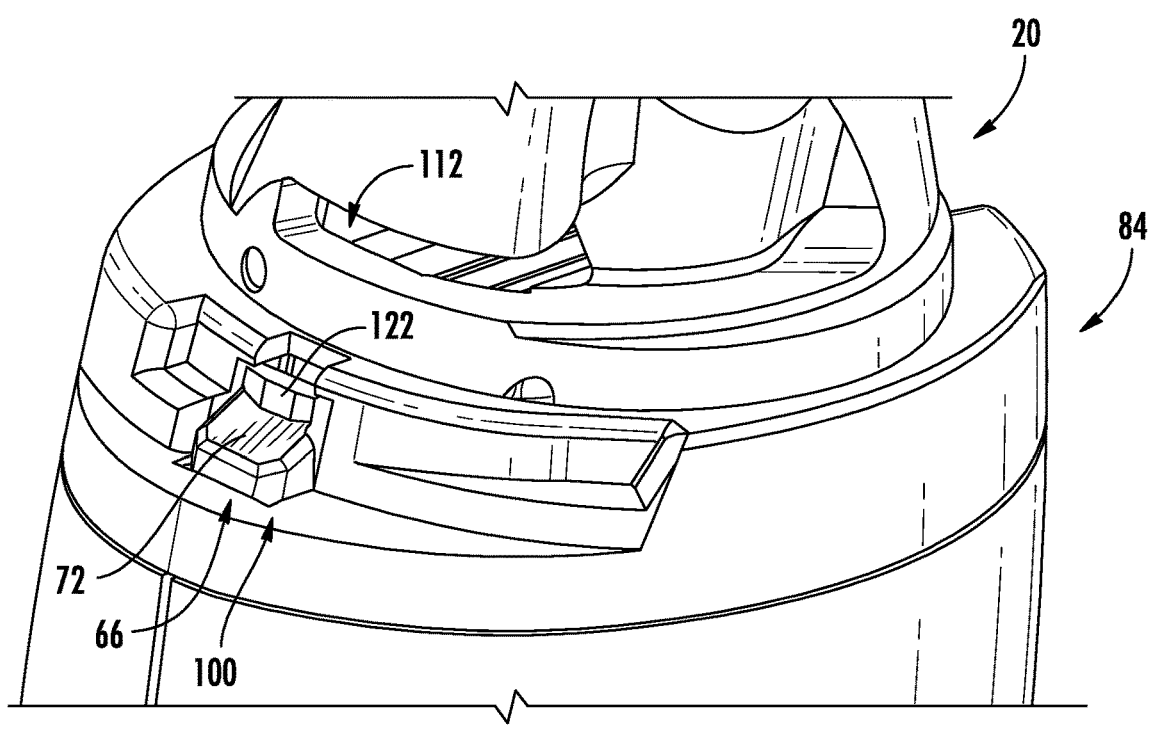
FIG. 7 is a detail perspective view of the applicator head of FIG. 5 connected to the outer housing of FIG. 2.

Referring now to FIGS. 5 and 6, more detailed views of the applicator head 20 in isolation are illustrated. The applicator head 20 includes a pair of outer housing engagement structures 100 and 102 in the form of openings at opposite sides of the socket portion 84. The openings 100 and 102 are sized and located to removably receive the heads 72 of the applicator head engagement structures 66 and 68. In particular, movement of the applicator head 20 toward the outer housing 12 causes the heads 72 of the applicator head engagement structures 66 and 68 to enter the openings 100 and 102 and engage with engaging surfaces 104 and 106 thereby placing the applicator head 20 in an applicator head closed configuration, as illustrated by FIG. 7.

Figure 8:
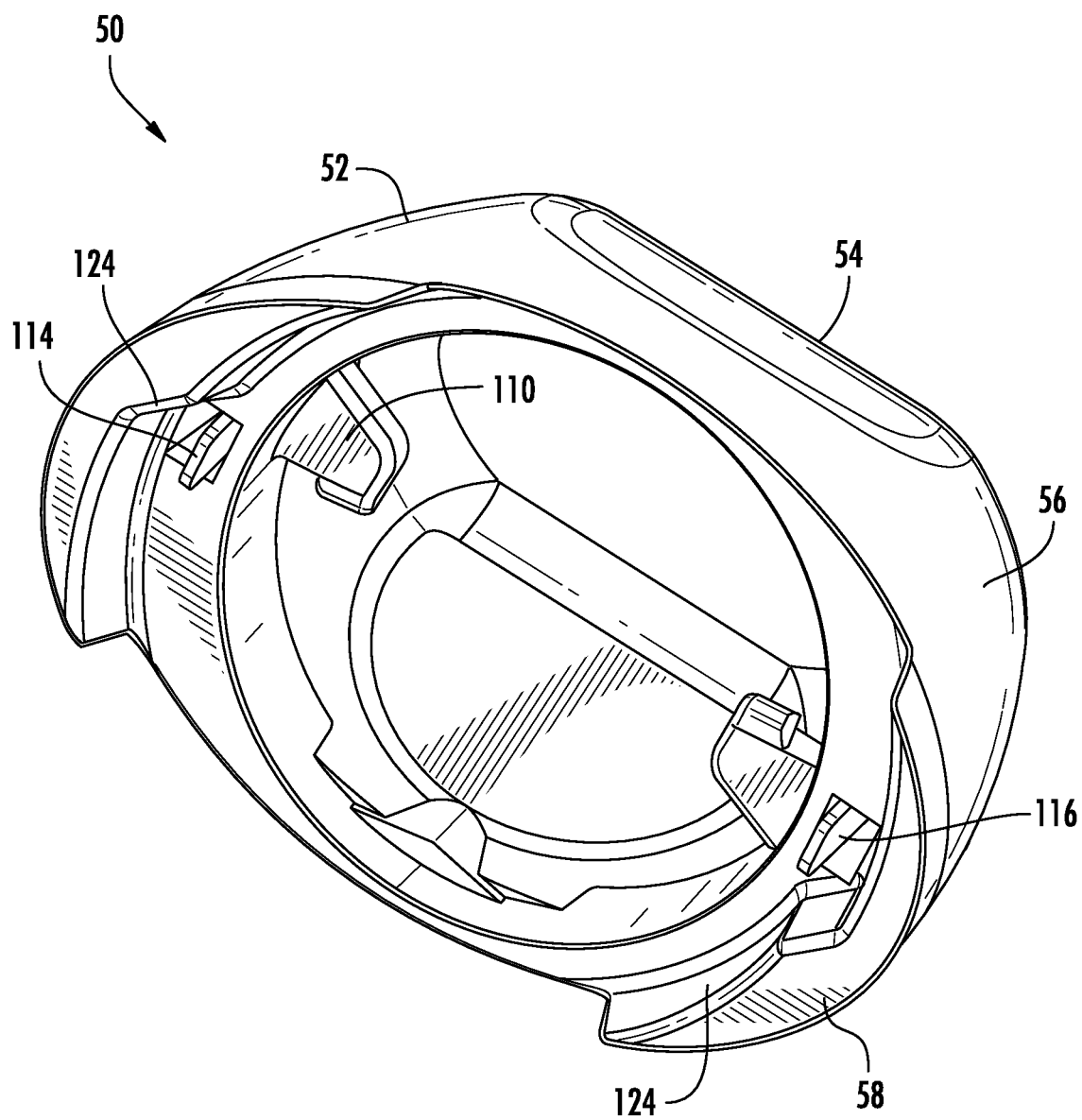
FIG. 8 is a bottom perspective view of a cap of the handheld treatment apparatus of FIG. 1, according to one or more embodiments shown and described herein.

Referring also to FIG. 8, the cap 50 includes the cap body 52 having the cover wall 54 and the side wall 56 that extends outward from the cover wall 54 to edge 58. The cap 50 includes a pair of head engagement projections 110 that engage a pair of cap engagement structures 112 with the cap in a cap closed and locked configuration. In the illustrated example, the head engagement projections 110 are in the form of hooks that can be received by the cap engagement structures 112 in the form of slots formed in the head portion 82 of the applicator head 20. The cap 50 further includes elastic tongues 114 and 116 that can be removably received by cap locking indents 118 and 120 that are provided adjacent the openings 100 and 102. The elastic tongues 114 and 116 inhibit rotation of the cap 50 relative to the applicator head 20 with the cap in the cap closed and locked configuration. However, the applicator head engagement structures 66 and 68 include a tongue engagement projection 122 that pushes the elastic tongues 114 and 116 out of the cap locking indents 118 and 120 with the heads 72 of the applicator head engagement structures 66 and 68 inserted through the openings 100 and 102 (FIG. 7). This places the cap 50 in a closed and unlocked configuration to allow for rotation of the cap 50 relative to the applicator head 20 in order to remove the cap 50 from the applicator head 20. In this regard, removal of the cap 50 from the applicator head 20 is dependent on connecting the applicator head 20 to the outer housing 12.

For removing the cartridge assembly 80 from the outer housing 12, the cap 50 includes a hook engagement surface 124 having a ramp shape that presses laterally on the heads 72 of the applicator head engagement structures 66 and 68 and moves them out of engagement with the engaging surfaces 104 and 106 as the cap 50 is rotated into the closed and locked configuration. In this regard, the cartridge assembly 80 can be removed from the outer housing 12 only when the cap 50 is in the closed and locked configuration. Removing the cartridge assembly 80 from the outer housing 12 allows the elastic tongues 114 and 116 to snap back into the cap locking indents 118 and 120 to prevent rotation of the cap 50 relative to the applicator head 20.

Nozzle Sealing and Unsealing

In consumer applications there is a high need for reliable performance with minimal effort from the consumer. Because of this, existing consumer printing devices may contain sophisticated processes for maintaining a high print quality. For example, it is common for consumer inkjet printing devices to contain hundreds of individual nozzles with each nozzle as small as 5-50 microns. Additionally, most compositions in such devices are volatile and are prone to drying out quickly when exposed to air. Due to the small and numerous nozzles and fast dry times, it may be difficult to keep all nozzles working properly over the course of use and potentially long periods of time between uses.

Figure 9:
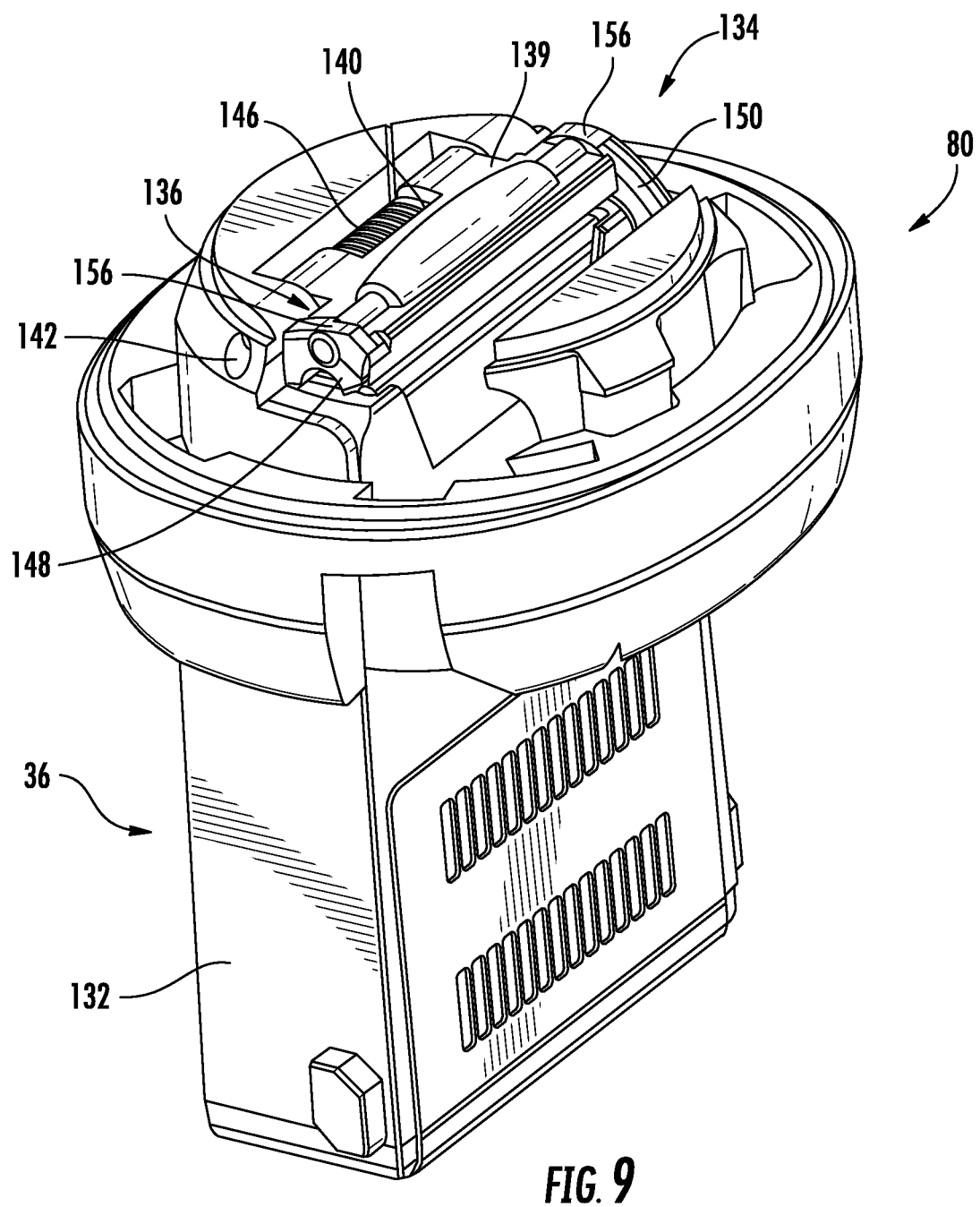
FIG. 9 is a perspective view of the cartridge assembly of FIG. 3 with the head portion removed to illustrate a sealing assembly, according to one or more embodiments shown and described herein.
Figure 10:
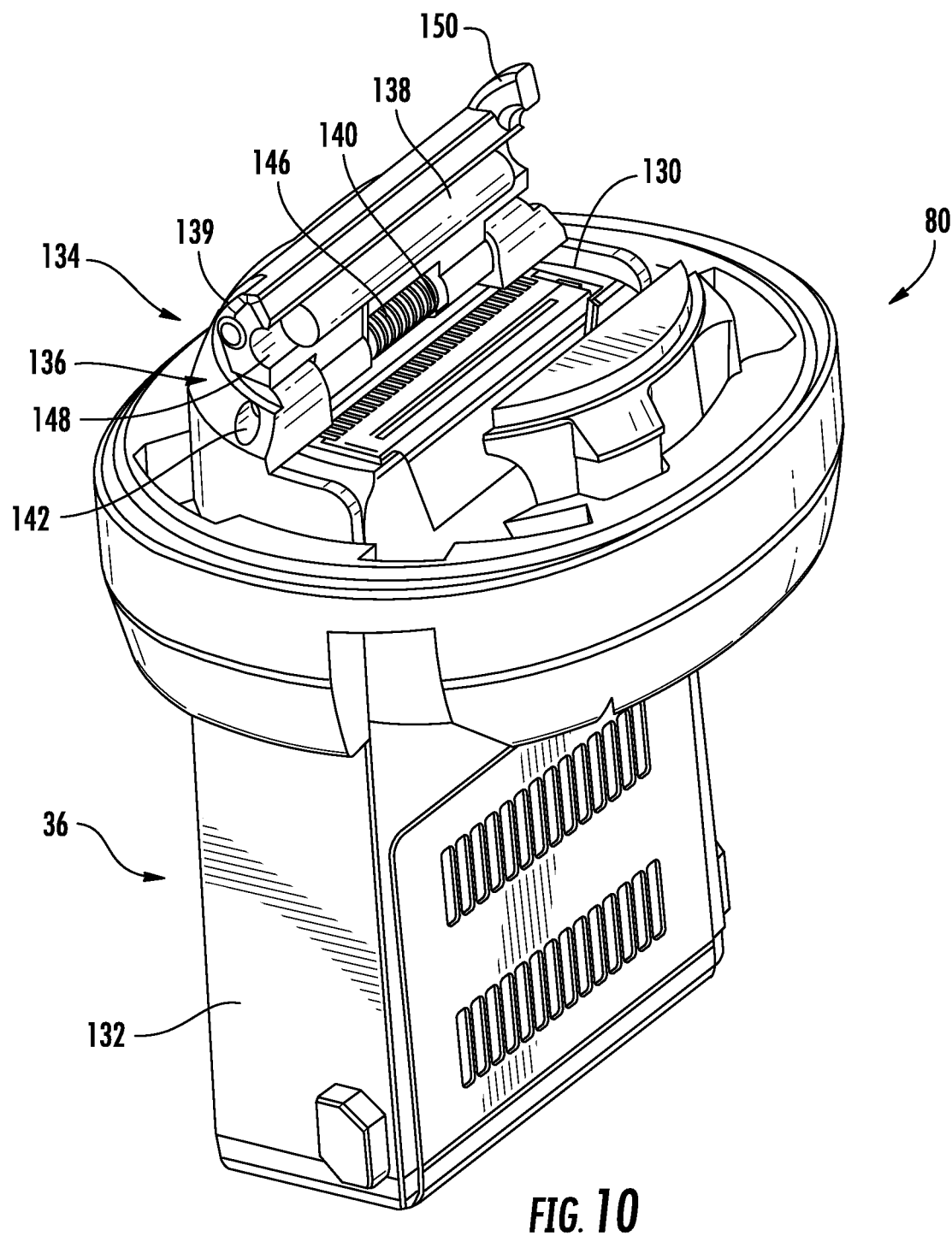
FIG. 10 is a perspective view of the sealing assembly of FIG. 9 in a open configuration, according to one or more embodiments shown and described herein.

Referring to FIGS. 9 and 10, the cartridge assembly 80 is illustrated with the applicator head 20 removed. As indicated above, the cartridge 36 includes an array of nozzles 130 and a housing 132 that is used as a reservoir for a skin treatment composition. The cartridge assembly 80 further includes a sealing assembly 134 that is used to seal the array of nozzles 130 with the cap 50 in the closed and locked configuration. In some embodiments, the sealing assembly 134 may hermetically seal the array of nozzles 130.

The sealing assembly 134 includes a support portion 136 that supports a resiliently deformable sealing element 138. The sealing element 138 may be formed using any suitable elastic material, such as plastic, foam, rubber and may be a 2-K molded part. For example, the support portion 136 and the sealing element 138 may be 2-K molded together to reduce cost. In the illustrated embodiment, the support portion 136 includes a frame 139 that is pivotally connected to the applicator head 20 by a pivot rod 140 that extends through a bore 142 at a lower edge of the frame 139. A helical spring 146 is wrapped around the pivot rod 140 to bias the frame 139 toward the illustrated open position. In another embodiment, instead of a helical spring, the sealing assembly might be moved by a feature within the cap 50. The frame 139 further includes a groove 148 that is sized to receive the sealing element 138. The groove 148 has a depth that is less than a width or diameter of the sealing element 138 such that a portion of the width of the sealing element 138 extends outward beyond the frame 139 in order to make intimate contact with the array of nozzles 130. In order to seal all of the nozzles 130, the sealing element may have a length that is at least the same or greater than a length of the array of nozzles 130. While the sealing element 138 is illustrated as cylindrical, the sealing element 138 may be any suitable shape or combination of shapes.

The sealing assembly 134 may further include a switch engaging element 150. The switch engaging element 150 extends laterally outward at an upper edge of the frame 139. In some embodiments, the switch engaging element 150 is sized to engage an activation switch 154 (FIG. 2) located within the outer housing 12 with the sealing assembly 134 in a closed configuration. The activation switch 154 provides a signal to the processing unit 30 to activate or deactivate based on whether or not the activation switch 154 is actuated by the switch engaging element 150. In particular, the processing unit 30 deactivates the handheld treatment apparatus 10 if the activation switch 154 is actuated by the switch engaging element 150 (in the closed configuration) and activates the handheld treatment apparatus 10 if the activation switch 154 is unactuated (in the open configuration). While a switch may be used, other devices may be used such as magnetic, optical, metal contacts, etc.

In the illustrated embodiment, the sealing assembly 134 is moved between the open configuration and the closed configuration using the cap 50. Referring again to FIGS. 5 and 6, the cap engagement structure 112 is in the form of slots that allow the head engagement projections 110 to extend therethrough (FIG. 8). The frame 139 has an engagement surface 156 that is located in the rotational path of the head engagement projection 110 such that the head engagement projection 110 engages the engagement surfaces 156 and pushes the sealing assembly 134 from the open configuration to the closed configuration as the cap 50 is rotated into the cap closed and locked configuration. The head engagement projection 110 further holds the sealing assembly 134 in the closed configuration while the cap 50 is in the closed and locked configuration. It should be noted that while the sealing assembly 134 is illustrated pivotally connected directly to the applicator head 20, the sealing assembly 134 may be connected directly to the cartridge 36.

Figure 11:
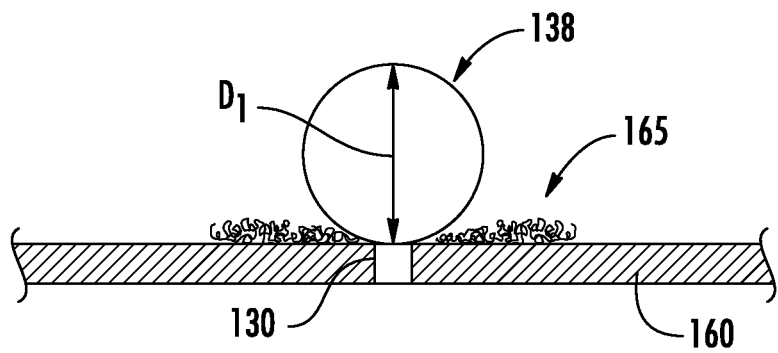
FIG. 11 illustrates a sealing element of the sealing assembly of FIG. 9 travelling toward a nozzle plate, according to one or more embodiments shown and described herein.
Figure 12:
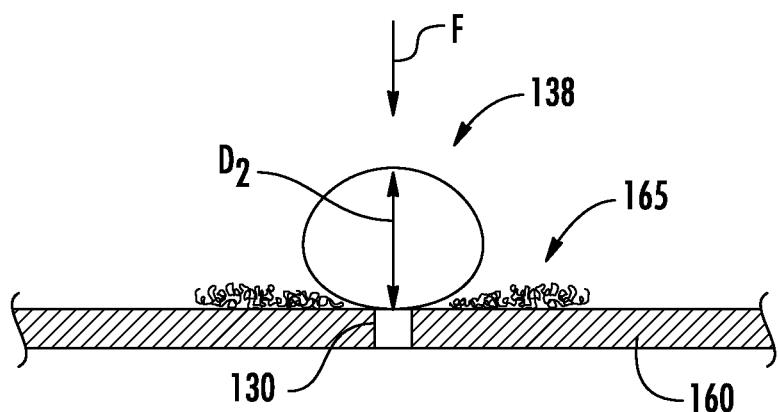
FIG. 12 illustrates the sealing element of FIG. 11 being forced against the nozzle plate, thereby reducing a width of the sealing element and increasing a contact area with the nozzle plate.
Figure 13:
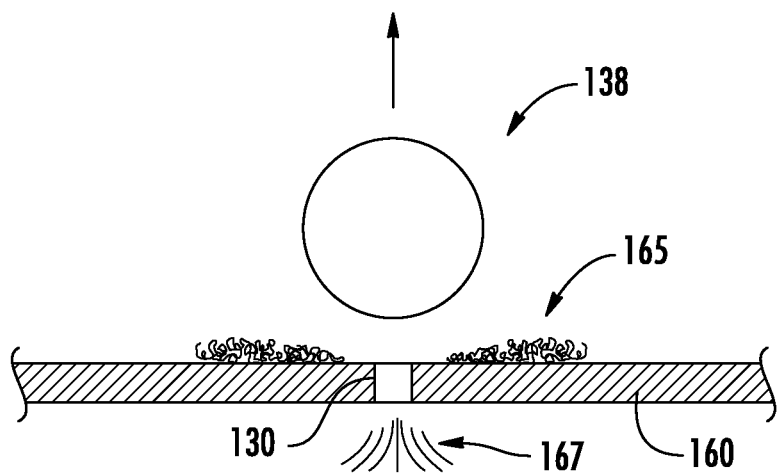
FIG. 13 illustrates the sealing element of FIG. 11 lifting away from the nozzle plate thereby priming the array of nozzles.

FIGS. 11-13 illustrate operation of the sealing element 138 when moving from the closed configuration (FIG. 12) to the opened configuration FIG. 13. Before contact with a nozzle plate 160 that houses the nozzles 130, the sealing element 138 has an original diameter $D_1$. A force F is applied against the sealing element 138, as described above, due to contact with the head engagement projection 110 with the cap 50 in the closed and locked configuration. Referring to FIG. 12, the sealing element 138 begins to deform and decrease a distance (e.g., no more than about 350 μm, such as no more than about 200 μm, such as no more than about 100 μm) in width to a diameter $D_2$ as the sealing element 138 comes into contact with the nozzle plate 160. As the sealing element 138 deforms, the amount of contact area and pressure between the sealing element 138 and the nozzle plate 160 increases on either side of the nozzles 130, thereby displacing debris 165 away from the nozzles 130. For example, this increase in contact area between the sealing element 138 and the nozzle plate 160 can provide a wiping motion that wipes the contact area around the nozzles 130, thereby displacing debris 165 away from the nozzles 130. For example, this increase in contact area between the sealing element 138 and the nozzle plate 160 can provide a squeezing motion that displacing debris 165 away from the nozzles 130. Referring to FIG. 13, as the sealing element 138 moves to the open configuration by travelling in a composition delivery direction away from the cartridge 36, the sealing element 138 resiliently returns to the original diameter D1 as the sealing element 138 is removed outwardly away from the nozzles 130 thereby providing decreased pressure at the nozzles 130, priming the nozzles 130 to aid in introduction of composition 167 to the nozzles 130.

Figure 14:
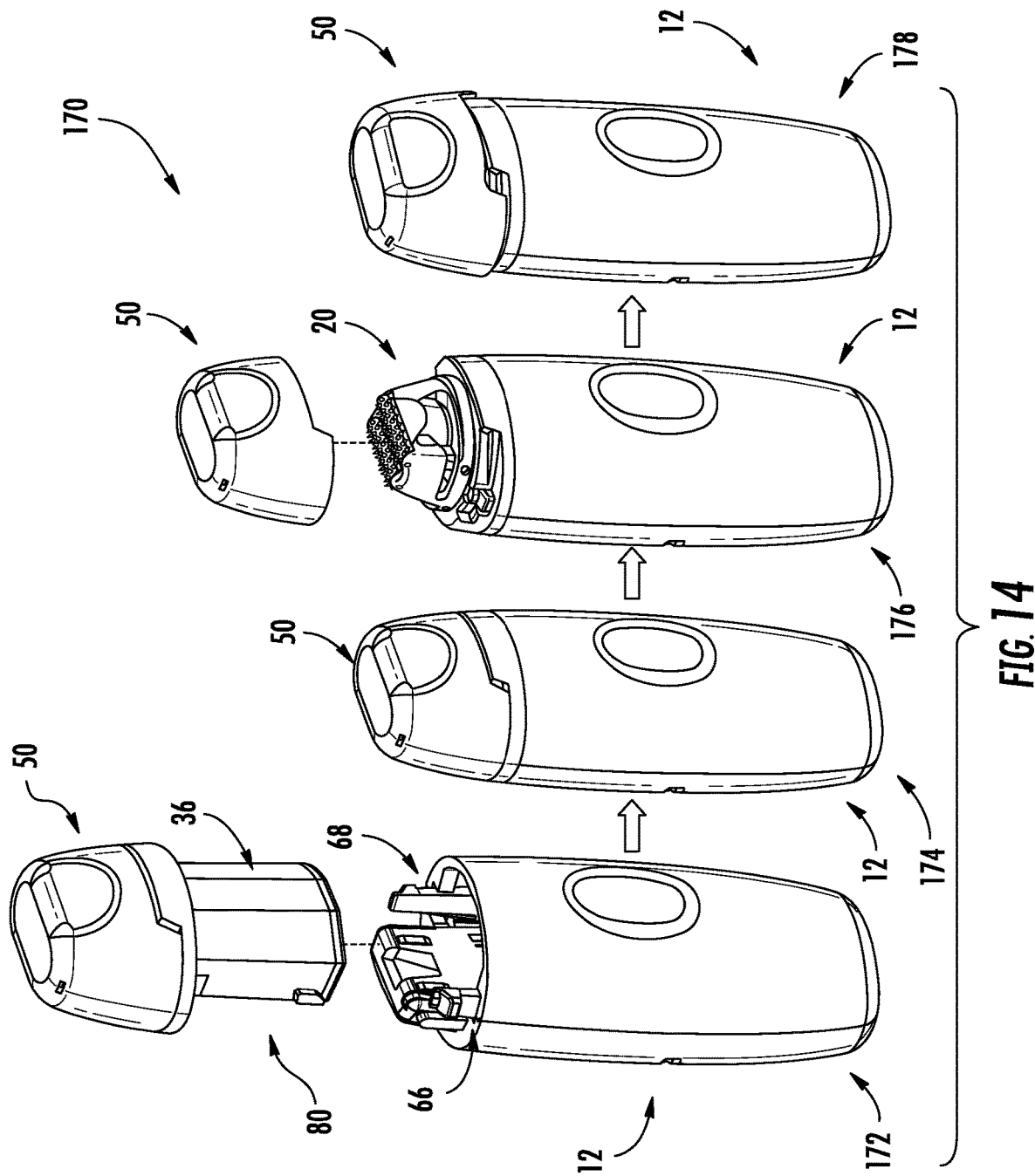
FIG. 14 illustrates a method of operating the handheld treatment apparatus of FIG. 1, according to one or more embodiments shown and described herein.

FIG. 14 illustrates a process 170 of using the handheld treatment apparatus 10 where, at step 172, the cartridge assembly 80 is located outside of the outer housing 12, the cartridge assembly 80 including the applicator head 20, cartridge 36 and cap 50. As illustrated, the cap 50 is in the closed and locked position and can only be removed when the cartridge assembly 80 is connected to the outer housing 12, as explained above. At step 174, inserting the cartridge 36 into the outer housing 12, the applicator head 20 locks to the outer housing 12 using the applicator head engagement structures 66 and 68. At the same time, the applicator head engagement structures 66 and 68 release the cap 50 to allow for rotation of the cap 50 relative to the applicator head 20.

At step 176, rotation of the cap 50 disengages the head engagement projections 110 and allows for removal of the cap 50 from the applicator head 20. At the same time, rotation of the cap 50 allows the sealing assembly 134 to move from the closed configuration to the open configuration due to the spring bias provided thereto and to also disengage activation switch 154, which can allow for activation of the nozzles 130. Step 178 illustrates cartridge assembly 80 removal by rotating the cap 50 in the opposite direction such that the hook engagement surfaces 124 move the applicator head engagement structures 66 and 68 to allow for removal of the cartridge assembly 80 from the outer housing 12. Then, the elastic tongues 114 and 116 move back into their cap locking indents 118 and 120 to inhibit rotation and removal of the cap 50 from the applicator head 20 while outside the outer housing 12.

General Operation

Operation of the handheld treatment apparatus 10 is directed to analyzing and treating tonal imperfections on human skin that comprises the steps of taking at least one background image of at least $10\mu^2$ of skin and then calculating the average background L value of the image on a grey scale. Further, a treatment image of the skin is acquired and from that image a localized L value is calculated for individual pixels or a group of pixels. The local L value is then compared to the background L value to identify skin deviations. A skin deviation is an area of skin where the difference between the two L values is greater than a predetermined $\Delta L$ value. The skin deviations are then treated with a treatment composition having a predetermined or variable contrast ratio.

The handheld treatment apparatus 10 has the applicator head 20 that includes the array of nozzles 130 and a reservoir (e.g., cartridge 36) for containing the skin treatment composition. The image capture device 46 can take an image of at least $10\mu^2$ of skin and the processing unit 30 can analyze the image to calculate the average background L value. The image capture device 46 then can take a subsequent image of the skin and calculate the localized L value of individual pixels or groups of pixels of skin. The processing unit 30 can then compare the local L value to the background L value to identify skin deviations where the difference between the two L values is greater than a predetermined value. While it is anticipated that a remote processing unit, either tethered to the device, or which communicates wirelessly, can be used, a local processing unit within the handheld treatment apparatus 10 is exemplified herein. Size and speed of the processing unit 30 can be an important consideration of the design parameters, but cost and other considerations can be considered.

The predetermined $\Delta L$ is the absolute value of the difference between the local L and the background L. This value, $\Delta L$, can be measured in absolute numbers or as a percentage. The images can be taken, or converted to a standard grey scale. Any numerical scale that measures lightness to darkness can be considered a "grey scale." Further, the background L value should not be too close to the ends of this scale. For example, if the grey scale is 0-100, with 0 being pure black and 100 being pure white, a background in the 0-10 range, or in the 90-100 range may be too light or too dark to show meaningful differences. Accordingly, one can adjust the background lighting, or the gain on the image capture device 46 taking the image, to move the background L closer to the middle of the scale. In this example, a background L of 50 would be ideal, with a background L in the range of 10-90 preferred, 20-80 even more preferred.

The most common grey scale is 0-255 (no units). In this example, it may be desirable to use image capture device and lighting settings that provide a background L value between 60 and 210. Using the 0-255 gray scale the $\Delta L$ may be at least 0.5, such as at least 1 and such as preferably at least 1.5, to initiate treatment of the skin. Likewise, $\Delta L$ can be measured as a percentage, for example, a numerical $\Delta L$ of 2.6 is approximately equal to 1.0% of a 255 grey scale. Thus, $\Delta L$ may be plus or minus 0.25%, such as plus or minus 0.5%, such as plus or minus 0.75%, of the grayscale.

The skin treatment compositions may be used to hide, or more appropriately, to camouflage a skin deviation. One characteristic of the skin treatment compositions is the contrast ratio. The contrast ratio of the treatment composition when treating the skin may be at least 0.1. The skin lightness and treatment composition lightness can be measured by a calibrated spectrophotometer. In the case of using a calibrated spectrophotometer, the average L value of human skin usually spans the range of about 25 to 75. In this case the corresponding treatment composition has a lightness value of at least 2 units greater, such as at least 3 units greater, and such as at least 5 units greater than the average skin lightness value of the consumer.

Images may be taken in sequence or preferably continuously. For example, a camera that takes a minimum of 4 frames per second may be used. Higher speed cameras (greater than 4 frames per second) may also be used. All images may be taken in a grey scale or converted to a grey scale, the grey scale can have any range, for example, 0-255, no units.

There is no technical difference between an image used for background L values and those used for local L values, the difference is in the analysis of the image. Hence, the images may be continually sent from the image capture device 46 to the processing unit 30 to calculate the L values, and $\Delta L$ values. It is understood, that the background L can be calculated once in a treatment period and that value reused throughout the treatment period. Or, it can be continually recalculated as long as the treatment process goes on. Moreover, there can be pre-programmed triggers to initiate a recalculation of the background L. For example, if an extended period of time elapses and no skin deviations are found, or if skin deviations are being found too frequently, a new background L might automatically be calculated.

When the $\Delta L$ exceeds the predetermined value, the skin deviation is treated with the treatment composition. Treatment requires firing one or more of the nozzles of the nozzle array 130 which dispense the treatment composition onto the skin in the area of the skin deviation. The treatment composition may be applied to the skin deviations in a discontinuous deposition pattern of discrete droplets between about $1\mu$ to about $100\mu$ in size. No more than 85% of the skin deviation may be covered by the treatment composition. More specifically, the treatment composition is applied via the linear array of nozzles 130 and the local L is calculated along the length of, and in the firing range of, the array of nozzles 130. An individual nozzle may be fired to deposit the treatment composition, or multiple nozzles fired at the same time. The number of nozzles fired along the linear array of nozzles 130 can be adjusted based on the size of the $\Delta L$ and the size of the skin deviation. Furthermore the frequency of nozzle firing can be adjusted based on the $\Delta L$, with more droplets being fired in succession in response to larger $\Delta L$ values. Additional details can be found in U.S. Pat. No. 9,949,552, filed Jul. 23, 2015, the details of which are hereby incorporated by reference as if fully set forth herein.

Figure 15:
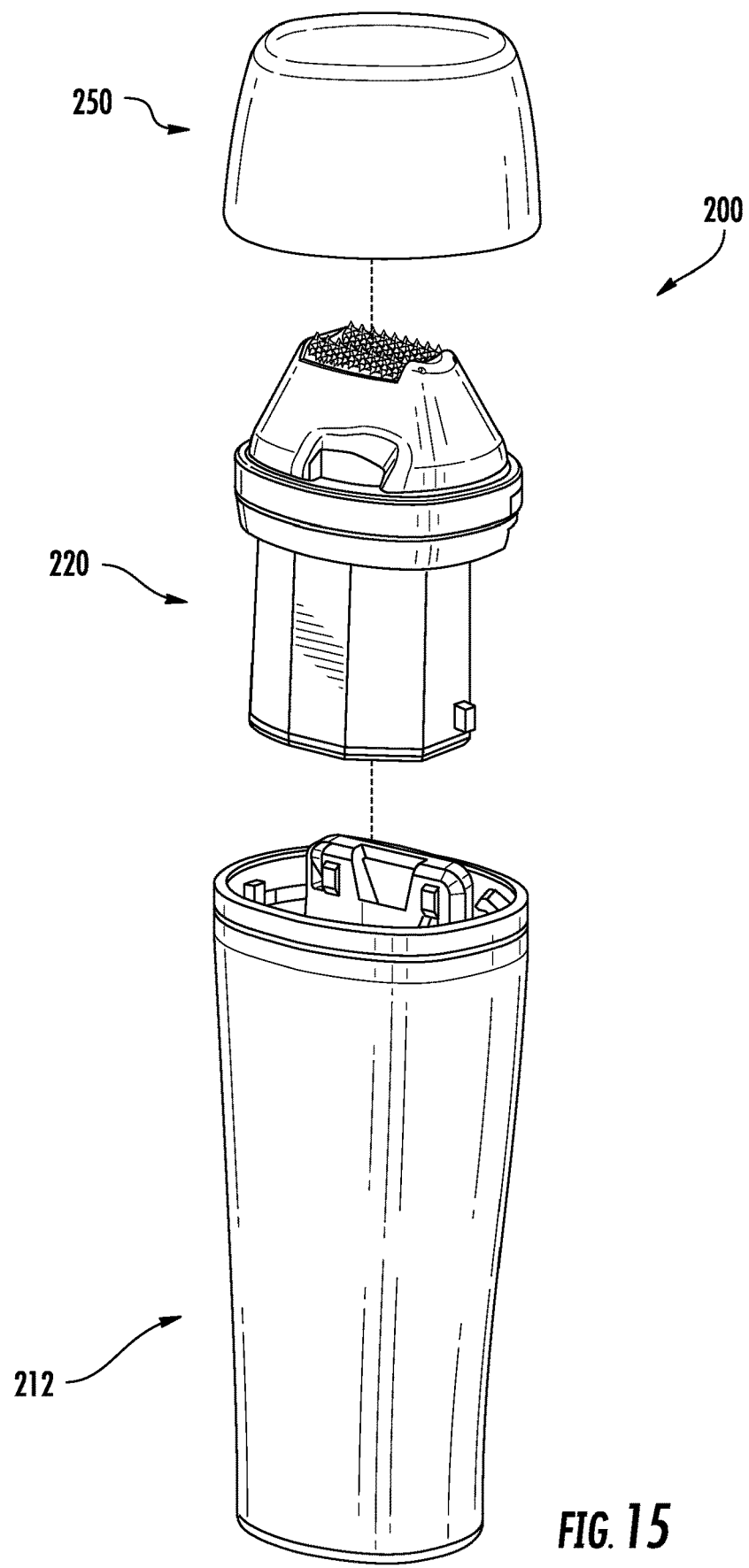
FIG. 15 is a perspective view of another handheld treatment apparatus, according to one or more embodiments shown and described herein.

Referring now to FIG. 15, another embodiment of a handheld treatment apparatus 200 is illustrated. The handheld treatment apparatus 200 includes many of the features of the handheld apparatus of FIG. 1 including an outer housing 212, an applicator head 220 and a cap 250 that removably connects to the applicator head 220 and outer housing 212. Generally and as above, the cap 250 can be removed from the applicator head 220 when cartridge assembly 280 is connected to the outer housing 212. Further, the cartridge assembly 280 can be removed from the outer housing 212 when the cap 250 is in a closed and locked configuration.

Figure 16:
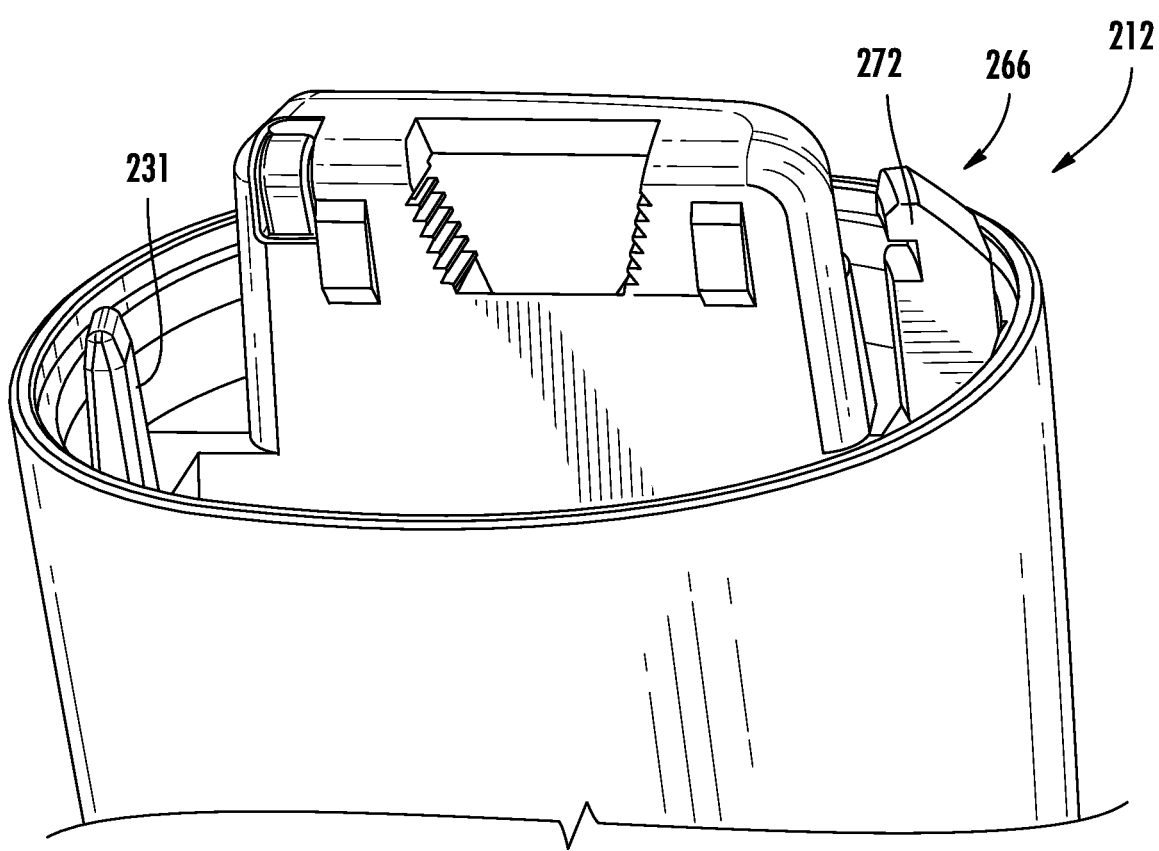
FIG. 16 is a perspective view of an outer housing of the handheld treatment apparatus, according to one or more embodiments shown and described herein.

Referring to FIG. 16, the outer housing 212 is illustrated without the applicator head 220, cartridge 236 and cap 250. In this embodiment, the outer housing 212 includes an applicator head engagement structure 266 in the form of a hook member that includes a head 272 that is arranged to engage the applicator head 220.

Figure 17:
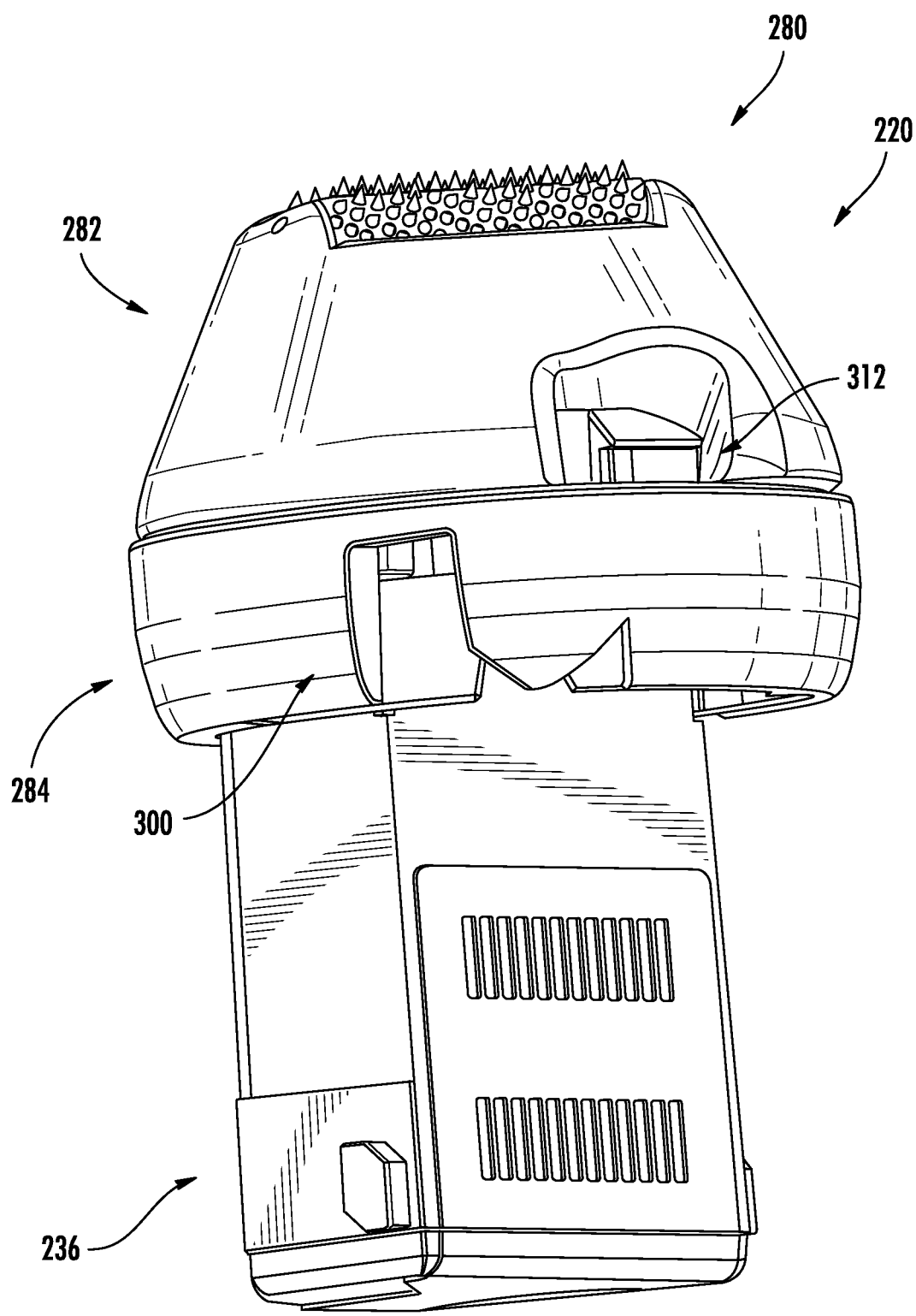
FIG. 17 is a perspective view of a cartridge assembly of the handheld treatment apparatus of FIG. 15, according to one or more embodiments shown and described herein.
Figure 18:
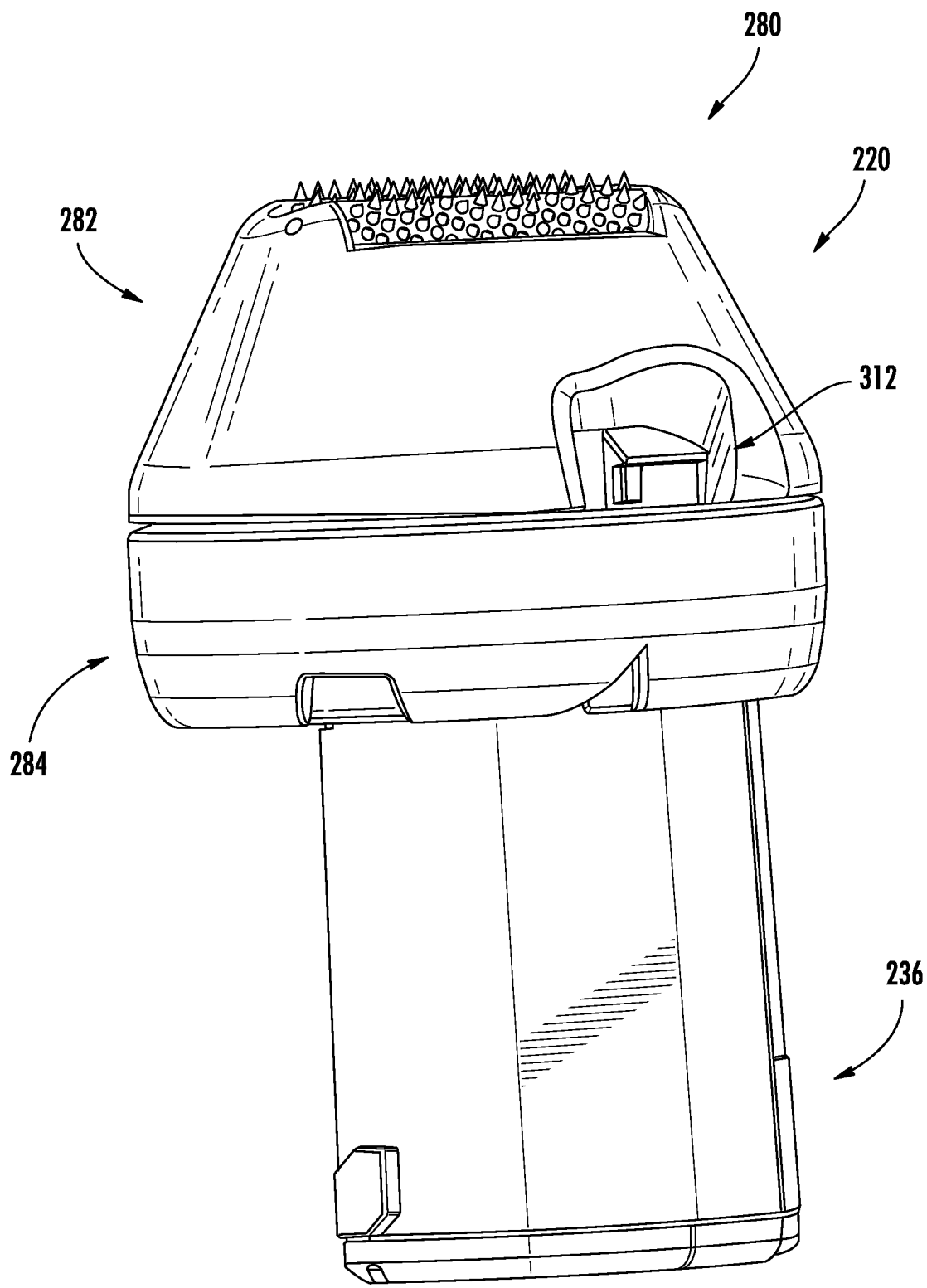
FIG. 18 is another perspective view of the cartridge assembly of FIG. 17.

Referring to FIGS. 17 and 18, more detailed views of the applicator head 220 along with the cartridge 236 are illustrated. The applicator head 220, in this embodiment, generally includes a head portion 282 and a socket portion 284 that is rotatably connected to the head portion 282 such that the head portion 282 can rotate relative to the socket portion 284. The socket portion 284 includes an outer housing engagement structure 300 in the form of an opening that is sized and shaped to removably receive the head 272 of the applicator head engagement structure 266. In particular, movement of the applicator head 220 toward the outer housing 212 causes the head 272 of the applicator head engagement structure 266 to enter the opening 300.

Figure 19:
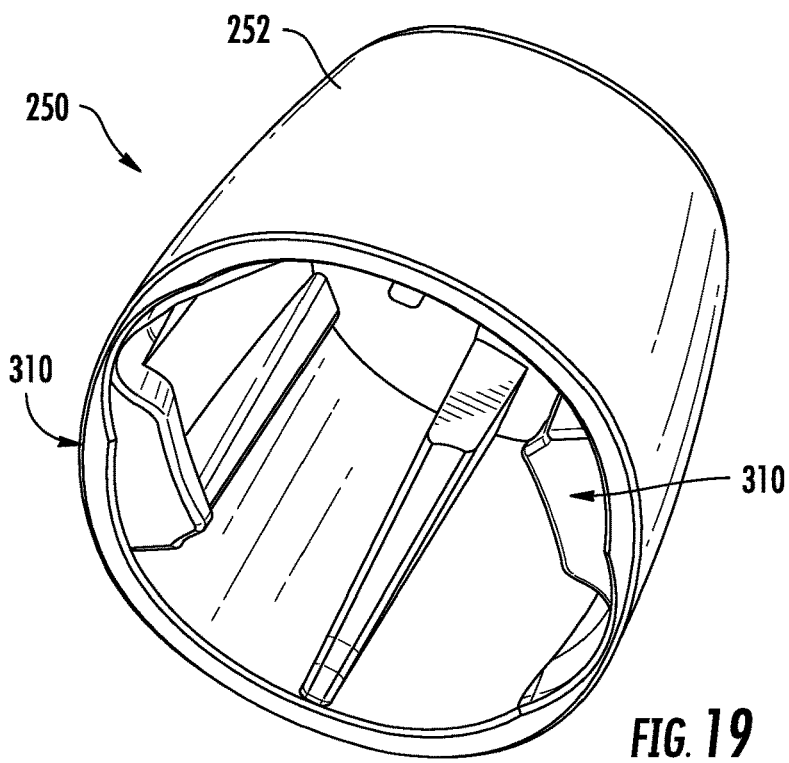
FIG. 19 is a bottom view of a cap of the handheld treatment apparatus of FIG. 15, according to one or more embodiments shown and described herein.

Referring also to FIG. 19, the cap 250 includes a cap body 252 that includes a pair of head engagement projections 310 that engage a pair of cap engagement structures 312 with the cap 250 in a closed and locked configuration. In the illustrated example, the head engagement projections 310 are in the form of ribs that can be received by the cap engagement structures 312 in the form of hooks formed in the head portion 282 of the applicator head 220. The shape of the head portion 282 is somewhat oblong thereby inhibiting rotation of the cap 250 relative to the head portion 282 due to the complimentary shape of the cap 250.

Figure 20:
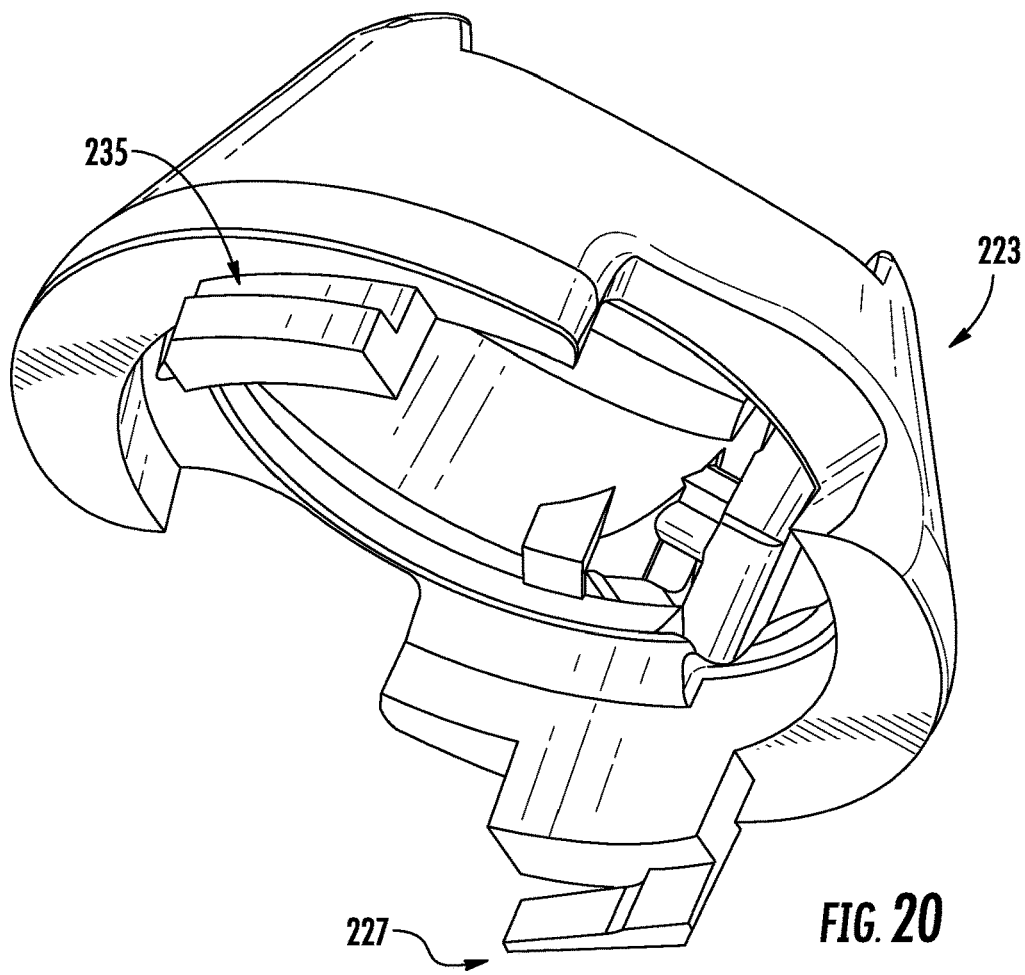
FIG. 20 is a bottom perspective view of a head portion of an applicator head of the handheld treatment apparatus of FIG. 15, according to one or more embodiments shown and described herein.
Figure 21:
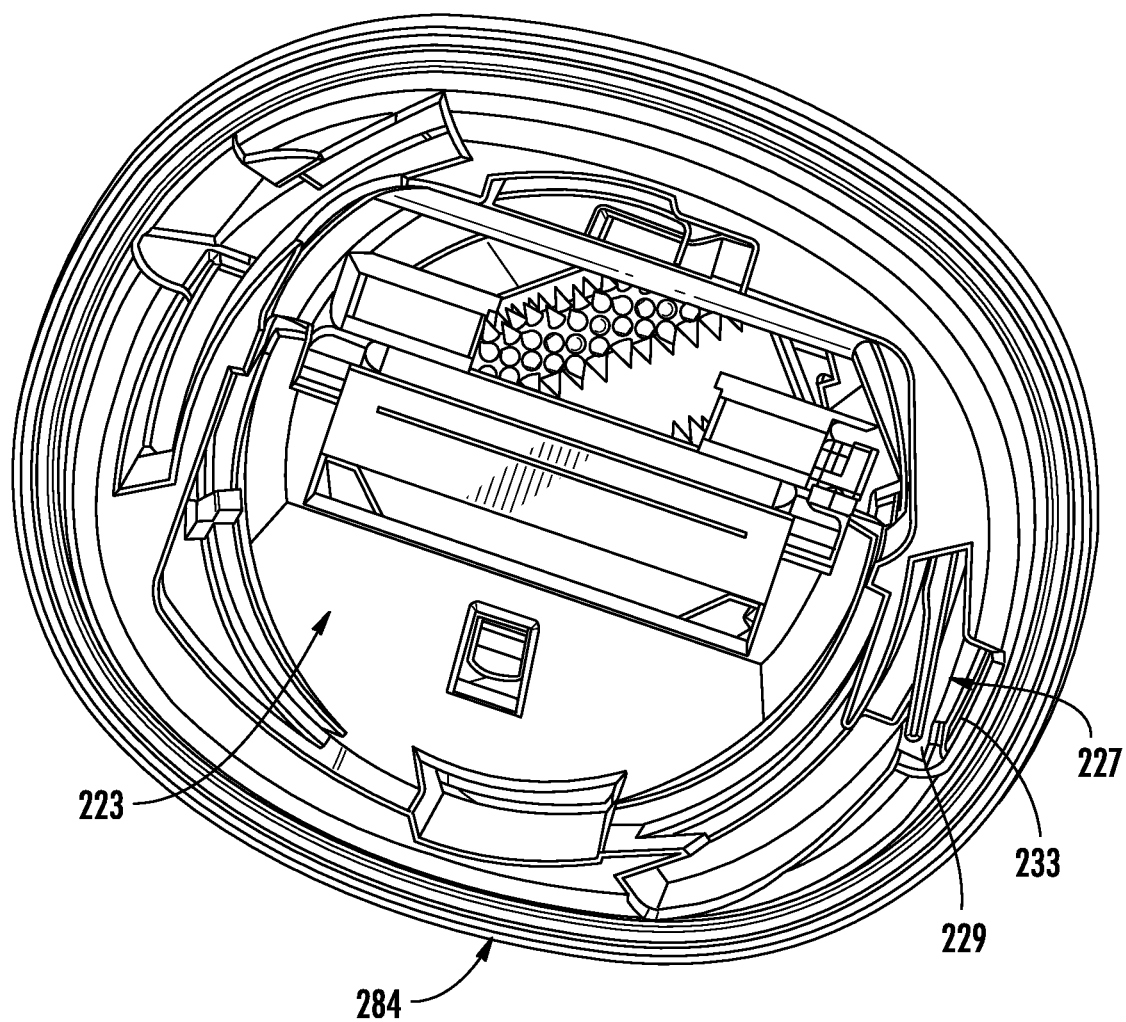
FIG. 21 is a bottom view of an applicator head of the handheld treatment apparatus of FIG. 15, according to one or more embodiments shown and described herein.

The head portion 282 and the cap 250 are inhibited from rotating relative to the socket portion 284 with the cartridge assembly 280 removed from the outer housing 212. In particular, referring to FIGS. 20 and 21, the head portion 282 includes an elastic tongue 227 that engages a locking surface 229 of the socket portion 284. When the cartridge assembly 280 is inserted into the outer housing 212, a release tongue 231 located in the outer housing 212 reaches through an opening 233 and moves the elastic tongue 227 out of engagement with the locking surface 229, thereby releasing the head portion 282 to be rotated relative to the socket portion 284. Rotating the cap 250 with the head portion 282 relative to the socket portion 284 counterclockwise positions a housing engagement structure 235 into engagement with the head 272 of the applicator head engagement structure 266 located in the opening 300 thereby locking the applicator head 220 to the outer housing 212 and allowing the cap 250 to be removed. Further, rotating the cap 250 to open position moves the engagement projections 310 out of engagement with engagement structures 312.

For removing the cartridge assembly 280 from the outer housing 212, the cap 250 can be placed on the applicator head 220 and rotated clockwise, which locks the cap 250 to the applicator head 220 using the head engagement projections 310 and cap engagement structures 312 and rotates the head portion 282 relative to the socket portion 284. This clockwise rotation of the head portion 282 removes the housing engagement structure 235 from engagement with the applicator head engagement structure 266 thereby allowing removal of the applicator head 220 from the outer housing 212, which also re-engages the elastic tongue 227 with the locking surface 229, thereby inhibiting rotation of the head portion 282 relative to the socket portion 284.

Figure 22:
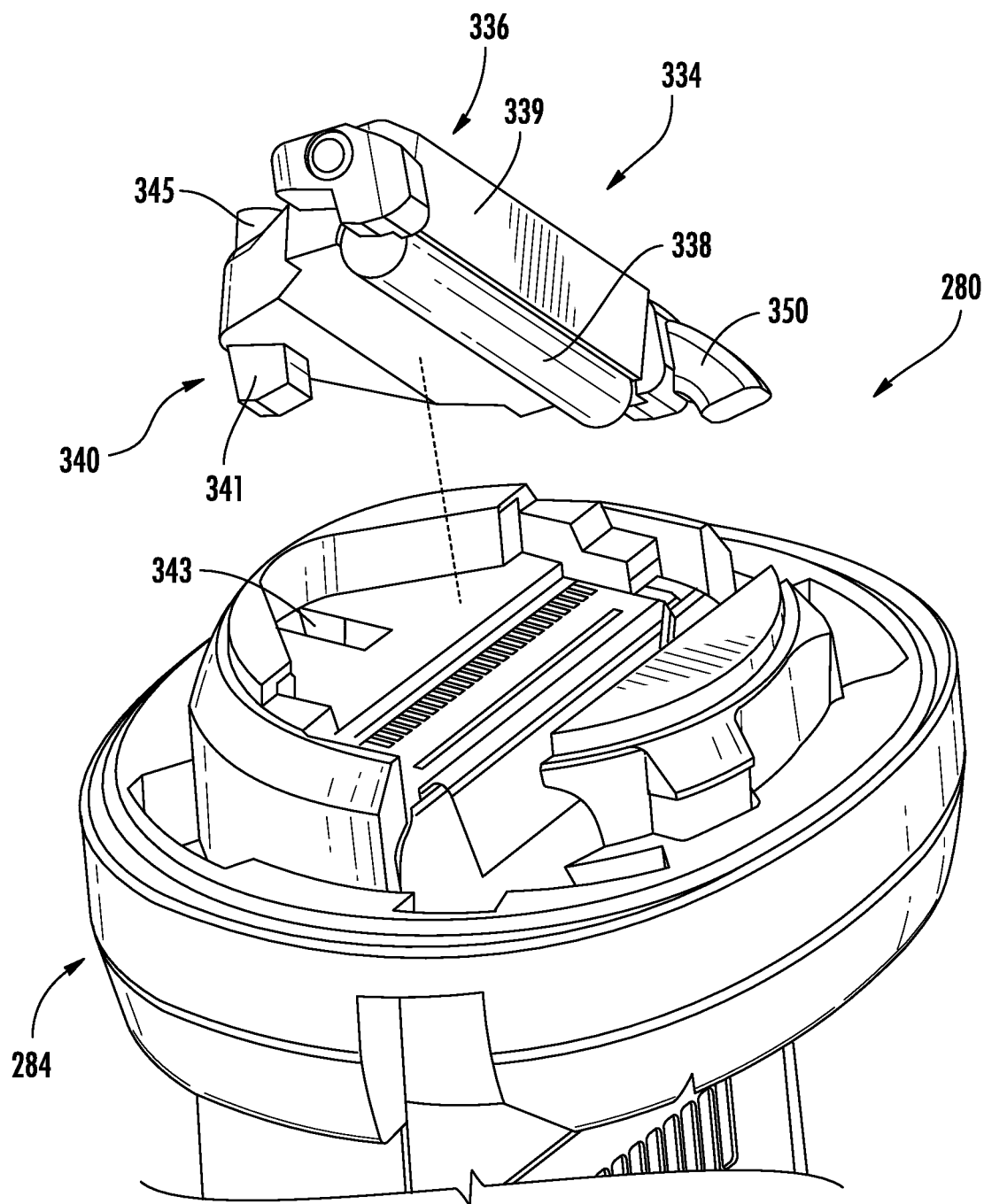
FIG. 22 is an exploded view of the cartridge assembly of FIG. 17 with the head portion of FIG. 20 removed to illustrate a sealing assembly, according to one or more embodiments shown and described herein.

Referring to FIG. 22, the cartridge assembly 280 is illustrated with the head portion 282 removed illustrating a sealing assembly 334 separated from the socket portion 284 for illustration. The sealing assembly 334 includes a support portion 336 and a resiliently deformable sealing element 338. In this embodiment, the sealing assembly 334 swivels, thus moving the sealing element 338 in a composition delivery direction and slides in the lateral direction (i.e., parallel to a plane containing array of nozzles 330) between a closed position and an open position depending on the rotational position of the head portion 282 of the applicator head 220.

Figure 23:
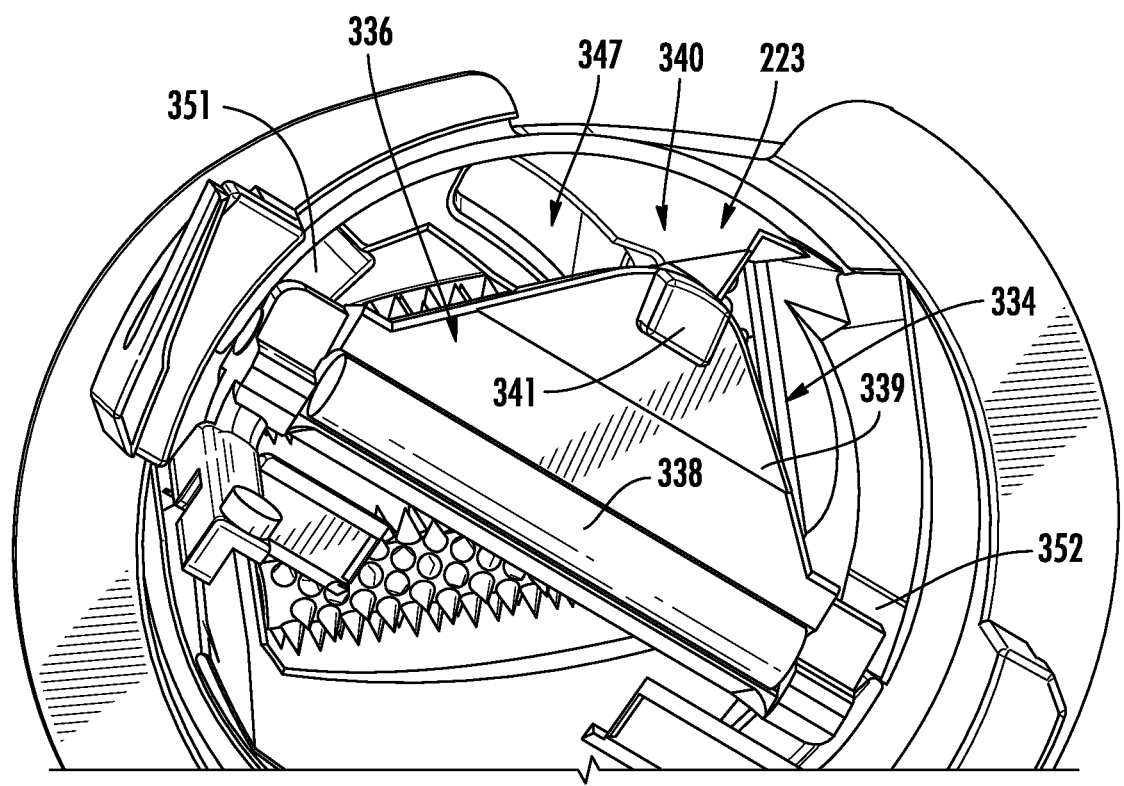
FIG. 23 is a bottom detail view of the head portion of FIG. 20.
Figure 24:
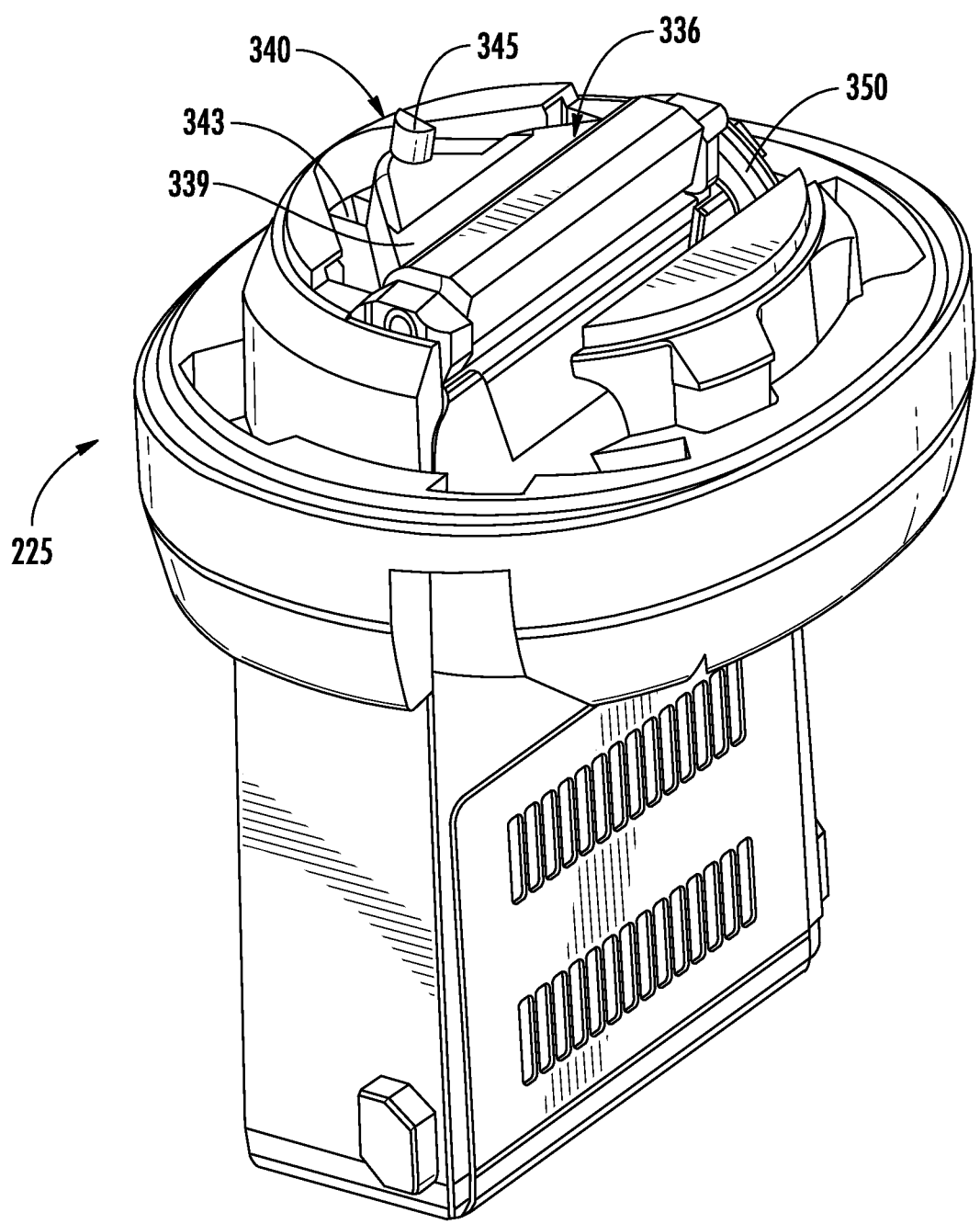
FIG. 24 is a perspective view of the cartridge assembly of FIG. 17 with the head portion removed to illustrate the sealing assembly in a closed configuration.
Figure 25:
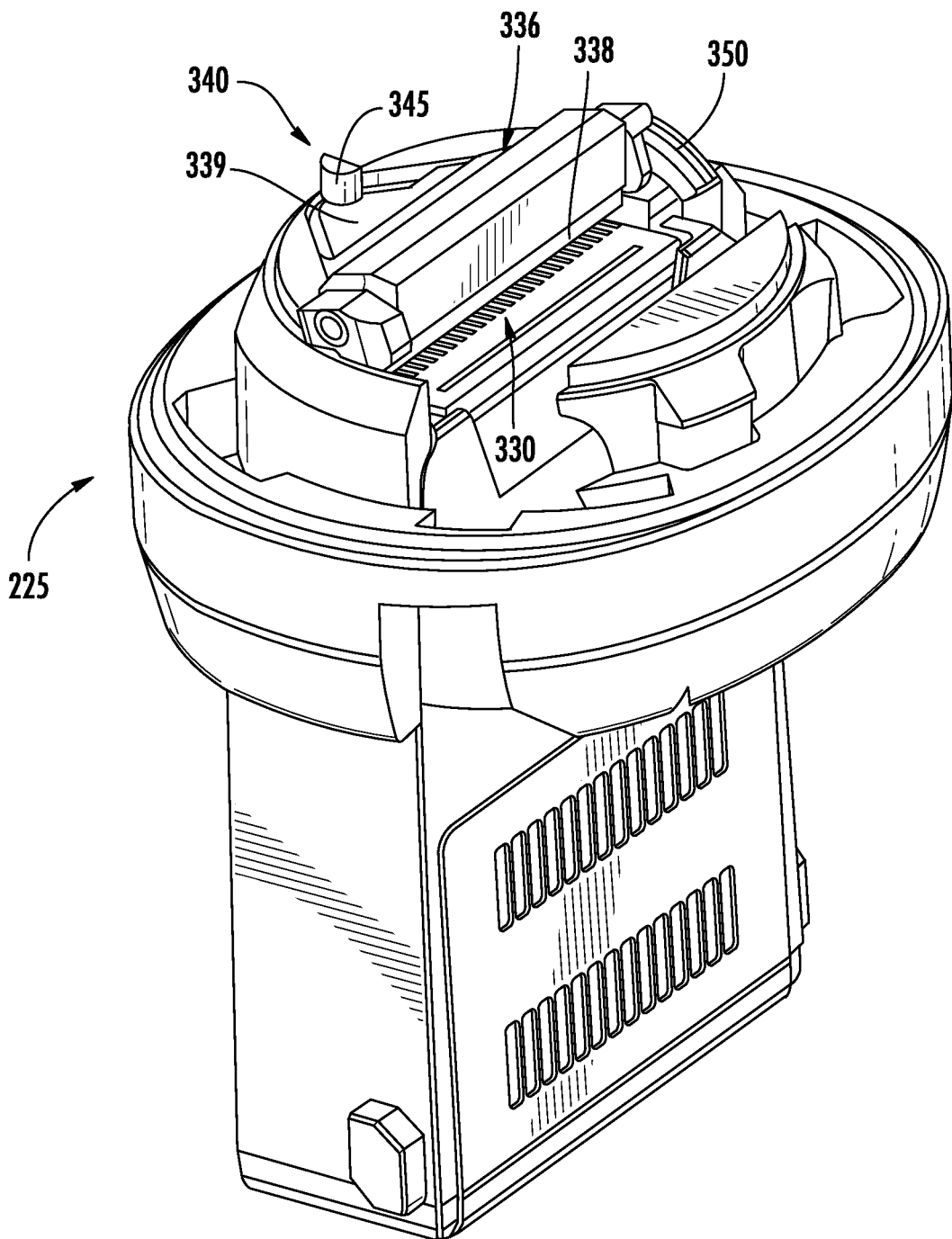
FIG. 25 is a perspective view of the cartridge assembly of FIG. 17 with the head portion removed to illustrate the sealing assembly in an open configuration.

Referring also to FIGS. 23 and 24, the support portion 336 includes a frame 339 that is slidably connected to the socket portion 284 by a guide pin 340. The guide pin 340 includes a portion 341 that is slidably received in a guide slot 343 provided by the socket portion 284. The guide pin 340 further includes a portion 345 that is slidably received within a drive slot 347 that is provided by the head portion 223. As the head portion 282 is rotated, as discussed above, the portion 345 moves along the drive slot 347 such that the frame 339 translates from a closed configuration (FIG. 23) to an open configuration (FIG. 24) thereby removing the sealing element 338 from the array of nozzles 330. In the closed configuration, the head portion 282 includes pressing surfaces 351 and 352 that apply a force against the sealing assembly 334 toward the cartridge 236 to compress the sealing element 338 into the array of nozzles 330 in a fashion similar to that shown by FIG. 12. As can be seen by FIG. 25, the frame 339 includes a switch engaging element 350 that engages an activation switch in a manner similar to that described above.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiments disclosed, or in any combination with any other reference or references, teaches, suggests or discloses any such embodiments. Further, to the extent that any meaning or definition of a term in this document conflicts with any meaning or definition of the same term in a document incorporated by reference, the meaning or definition assigned to that term in this document shall govern.

While particular embodiments have been illustrated and described, it would be obvious to those skilled in the art that various other changes and modifications can be made without departing from the spirit and scope of the claims. It is therefore intended to cover in the appended claims all such changes and modifications that are within the scope of this specification.

What is claimed is:

1. An apparatus for treating human skin, comprising:
an outer housing including a graspable portion;
an applicator head;
a cartridge connected to the applicator head, the cartridge comprising a nozzle located in the applicator head;
an image capture device that captures images of the human skin through an opening in the applicator head;
a processor that analyzes the images of the human skin to identify skin deviations;
a sealing assembly comprising a support portion and a resiliently deformable sealing element supported by the support portion at a location within the applicator head, the sealing assembly having a closed configuration where the sealing element is sealed against the nozzle and an open configuration where the sealing element is removed outward away from the nozzle in a composition delivery direction to expose the nozzle for operation; and,
wherein the sealing assembly has the closed configuration with the cartridge assembly removed from the outer housing and the open configuration with the cartridge assembly connected to the outer housing.

2. The apparatus of claim 1, wherein the sealing assembly is moveably connected to the outer housing.

3. The apparatus of claim 1, wherein the sealing assembly is moveably connected to the applicator head.

4. The apparatus of claim 1, wherein the sealing assembly is moveably connected to the cartridge.

5. The apparatus of claim 1, wherein the cartridge comprises a skin treatment composition for use in treating human skin.

6. The apparatus of claim 1, wherein the sealing element resiliently deforms against the nozzle from an original shape thereby pushing debris away from the nozzle as the sealing assembly is placed in the closed configuration.

7. The apparatus of claim 6, wherein the sealing element returns toward the original shape as the sealing assembly is placed in the open configuration thereby providing a decrease in pressure at the nozzle.

8. The apparatus of claim 1, wherein the cartridge comprises multiple nozzles and the sealing element is sized to seal against the multiple nozzles with the sealing assembly in the closed configuration.

9. The apparatus of claim 1, wherein the sealing assembly comprises a switch engaging element that actuates an activation switch as the sealing assembly moves from the closed configuration to the open configuration.

10. The apparatus of claim 1, wherein the sealing element deforms from an original dimension a distance of no more than 350 μm against the nozzle with the sealing assembly in the closed configuration.

11. The apparatus of claim 1 further comprising a cap that releasably engages the applicator head.

12. The apparatus of claim 11, wherein the support portion of the sealing assembly comprises a cap engagement element, the cap engagement element arranged to engage a cooperating sealing engagement element located within the cap with the cap in a closed and locked configuration, the sealing engagement element applying a force in a direction toward the cartridge in the closed and locked configuration.

13. The apparatus of claim 12, wherein the cap has an open configuration where the sealing engagement element is moved out of engagement with the cap engagement element to allow the sealing element to be removed from the nozzle to expose the nozzle for operation.

* * * * *